United States Patent
Neundorf et al.

(10) Patent No.: US 9,417,056 B2
(45) Date of Patent: Aug. 16, 2016

(54) DEVICE FOR OPTICALLY SCANNING AND MEASURING AN ENVIRONMENT

(71) Applicant: FARO Technologies, Inc., Lake Mary, FL (US)

(72) Inventors: Christoph Neundorf, Langewiesen (DE); Reinhard Becker, Ludwigsburg (DE)

(73) Assignee: FARO TECHNOLOGIES, INC., Lake Mary, FL (US)

( * ) Notice: Subject to any disclaimer, the term of this patent is extended or adjusted under 35 U.S.C. 154(b) by 97 days.

(21) Appl. No.: 14/374,054

(22) PCT Filed: Dec. 12, 2012

(86) PCT No.: PCT/EP2012/075178
§ 371 (c)(1),
(2) Date: Jul. 23, 2014

(87) PCT Pub. No.: WO2013/110402
PCT Pub. Date: Aug. 1, 2013

(65) Prior Publication Data
US 2015/0029516 A1   Jan. 29, 2015

(30) Foreign Application Priority Data

Jan. 25, 2012 (DE) .......................... 10 2012 100 609

(51) Int. Cl.
*G01N 11/14* (2006.01)
*G01N 21/47* (2006.01)
(Continued)

(52) U.S. Cl.
CPC .............. *G01B 11/14* (2013.01); *G01C 15/002* (2013.01); *G01N 21/47* (2013.01); *G02B 26/10* (2013.01); *G01N 2201/06113* (2013.01); *G01N 2201/105* (2013.01)

(58) Field of Classification Search
USPC .................... 356/237.1–241.6, 242.1–243.8, 356/426–431, 600–640
See application file for complete search history.

(56) References Cited

U.S. PATENT DOCUMENTS

| 1,535,312 A | 4/1925 | Hosking |
| 1,538,758 A | 5/1925 | Taylor |

(Continued)

FOREIGN PATENT DOCUMENTS

| AT | 508635 A1 | 3/2011 |
| AU | 2005200937 A1 | 9/2006 |

(Continued)

OTHER PUBLICATIONS

Laser Reverse Engineering with Microscribe, [online], [retrieved Nov. 29, 2011], http://www.youtube.com/watch?v=8VRz_2aEJ4E &feature=PlayList&p=F63ABF74F30DC81B&playnext=1 &playnext_from=PL&index=1.

(Continued)

*Primary Examiner* — Kara E Geisel
*Assistant Examiner* — Jarreas C Underwood
(74) *Attorney, Agent, or Firm* — Cantor Colburn LLP (57) ABSTRACT

A laser scanner device for optically scanning and measuring an environment includes a base, a measuring head which is rotatable relative to the base, and a mirror which is rotatably relative to the measuring head, wherein, in at least one operating mode, the laser scanner is mounted on a cart by a mounting device, the cart moves the base which is fixedly connected with the mounting device, the measuring head rests relative to the base, the mirror rotates, and the measuring head is locked with the mounting device by a locking mechanism.

7 Claims, 3 Drawing Sheets

(51) Int. Cl.
  *G02B 26/10* (2006.01)
  *G01B 11/14* (2006.01)
  *G01C 15/00* (2006.01)

(56) References Cited

U.S. PATENT DOCUMENTS

| | | |
|---|---|---|
| 1,918,813 A | 7/1933 | Kinzy |
| 2,316,573 A | 4/1943 | Egy |
| 2,333,243 A | 11/1943 | Glab |
| 2,702,683 A | 2/1955 | Green et al. |
| 2,748,926 A | 6/1956 | Leahy |
| 2,983,367 A | 6/1958 | Paramater et al. |
| 2,924,495 A | 9/1958 | Haines |
| 2,966,257 A | 12/1960 | Littlejohn |
| 3,066,790 A | 12/1962 | Armbruster |
| 3,447,852 A | 6/1969 | Barlow |
| 3,458,167 A | 7/1969 | Cooley, Jr. |
| 3,830,567 A | 8/1974 | Riegl |
| 3,899,145 A | 8/1975 | Stephenson |
| 3,945,729 A | 3/1976 | Rosen |
| 4,138,045 A | 2/1979 | Baker |
| 4,178,515 A | 12/1979 | Tarasevich |
| 4,340,008 A | 7/1982 | Mendelson |
| 4,379,461 A | 4/1983 | Nilsson et al. |
| 4,413,907 A * | 11/1983 | Lane ............ G01C 15/002 318/16 |
| 4,424,899 A | 1/1984 | Rosenberg |
| 4,430,796 A | 2/1984 | Nakagawa |
| 4,457,625 A | 7/1984 | Greenleaf et al. |
| 4,506,448 A | 3/1985 | Topping et al. |
| 4,537,233 A | 8/1985 | Vroonland et al. |
| 4,544,236 A * | 10/1985 | Endo ............... G02B 7/16 359/814 |
| 4,561,776 A | 12/1985 | Pryor |
| 4,606,696 A | 8/1986 | Slocum |
| 4,659,280 A | 4/1987 | Akeel |
| 4,663,852 A | 5/1987 | Guarini |
| 4,664,588 A | 5/1987 | Newell et al. |
| 4,667,231 A | 5/1987 | Pryor |
| 4,676,002 A | 6/1987 | Slocum |
| 4,714,339 A | 12/1987 | Lau et al. |
| 4,733,961 A | 3/1988 | Mooney |
| 4,736,218 A | 4/1988 | Kutman |
| 4,751,950 A | 6/1988 | Bock |
| 4,767,257 A | 8/1988 | Kato |
| 4,790,651 A | 12/1988 | Brown et al. |
| 4,816,822 A | 3/1989 | Vache et al. |
| 4,870,274 A | 9/1989 | Hebert et al. |
| 4,882,806 A | 11/1989 | Davis |
| 4,891,509 A | 1/1990 | Jones et al. |
| 4,954,952 A | 9/1990 | Ubhayakar et al. |
| 4,982,841 A | 1/1991 | Goedecke |
| 4,984,881 A | 1/1991 | Osada et al. |
| 4,996,909 A | 3/1991 | Vache et al. |
| 4,999,491 A | 3/1991 | Semler et al. |
| 5,021,641 A | 6/1991 | Swartz et al. |
| 5,025,966 A | 6/1991 | Potter |
| 5,027,951 A | 7/1991 | Johnson |
| 5,068,971 A | 12/1991 | Simon |
| 5,069,524 A | 12/1991 | Watanabe et al. |
| 5,155,684 A | 10/1992 | Burke et al. |
| 5,168,532 A | 12/1992 | Seppi et al. |
| 5,189,797 A | 3/1993 | Granger |
| 5,205,111 A | 4/1993 | Johnson |
| 5,211,476 A | 5/1993 | Coudroy |
| 5,212,738 A | 5/1993 | Chande et al. |
| 5,213,240 A | 5/1993 | Dietz et al. |
| 5,216,479 A | 6/1993 | Dotan et al. |
| 5,218,427 A | 6/1993 | Koch |
| 5,219,423 A | 6/1993 | Kamaya |
| 5,239,855 A | 8/1993 | Schleifer et al. |
| 5,289,264 A | 2/1994 | Steinbichler |
| 5,289,265 A | 2/1994 | Inoue et al. |
| 5,289,855 A | 3/1994 | Baker et al. |
| 5,313,261 A | 5/1994 | Leatham et al. |
| 5,319,445 A | 6/1994 | Fitts |
| 5,329,347 A | 7/1994 | Wallace et al. |
| 5,329,467 A | 7/1994 | Nagamune et al. |
| 5,332,315 A | 7/1994 | Baker et al. |
| 5,337,149 A | 8/1994 | Kozah et al. |
| 5,371,347 A | 12/1994 | Plesko |
| 5,372,250 A | 12/1994 | Johnson |
| 5,373,346 A | 12/1994 | Hocker |
| 5,402,365 A | 3/1995 | Kozikaro et al. |
| 5,402,582 A | 4/1995 | Raab |
| 5,412,880 A | 5/1995 | Raab |
| 5,416,505 A | 5/1995 | Eguchi et al. |
| 5,430,384 A | 7/1995 | Hocker |
| 5,446,846 A | 8/1995 | Lennartsson |
| 5,455,670 A | 10/1995 | Payne et al. |
| 5,455,993 A | 10/1995 | Link et al. |
| 5,510,977 A | 4/1996 | Raab |
| 5,517,297 A | 5/1996 | Stenton |
| 5,528,354 A | 6/1996 | Uwira |
| 5,528,505 A | 6/1996 | Granger et al. |
| 5,535,524 A | 7/1996 | Carrier et al. |
| 5,563,655 A | 10/1996 | Lathrop |
| 5,577,130 A | 11/1996 | Wu |
| 5,611,147 A | 3/1997 | Raab |
| 5,615,489 A | 4/1997 | Breyer et al. |
| 5,623,416 A | 4/1997 | Hocker, III |
| 5,629,756 A | 5/1997 | Kitajima |
| 5,668,631 A | 9/1997 | Norita et al. |
| 5,675,326 A | 10/1997 | Juds et al. |
| 5,677,760 A | 10/1997 | Mikami et al. |
| 5,682,508 A | 10/1997 | Hocker, III |
| 5,716,036 A | 2/1998 | Isobe et al. |
| 5,724,264 A | 3/1998 | Rosenberg et al. |
| 5,734,417 A | 3/1998 | Yamamoto et al. |
| 5,745,050 A * | 4/1998 | Nakagawa ........... G08G 1/16 180/167 |
| 5,745,225 A | 4/1998 | Watanabe et al. |
| 5,752,112 A | 5/1998 | Paddock et al. |
| 5,754,449 A | 5/1998 | Hoshal et al. |
| 5,768,792 A | 6/1998 | Raab |
| 5,793,993 A | 8/1998 | Broedner et al. |
| 5,804,805 A | 9/1998 | Koenck et al. |
| 5,825,666 A | 10/1998 | Freifeld |
| 5,829,148 A | 11/1998 | Eaton |
| 5,831,719 A | 11/1998 | Berg et al. |
| 5,832,416 A | 11/1998 | Anderson |
| 5,844,591 A | 12/1998 | Takamatsu et al. |
| 5,856,874 A | 1/1999 | Tachibana et al. |
| 5,887,122 A | 3/1999 | Terawaki et al. |
| 5,894,123 A | 4/1999 | Ohtomo et al. |
| 5,898,484 A | 4/1999 | Harris |
| 5,898,490 A | 4/1999 | Ohtomo et al. |
| 5,909,939 A | 6/1999 | Fugmann |
| 5,926,782 A | 7/1999 | Raab |
| 5,933,267 A | 8/1999 | Ishizuka |
| 5,936,721 A | 8/1999 | Ohtomo et al. |
| 5,940,170 A | 8/1999 | Berg et al. |
| 5,940,181 A | 8/1999 | Tsubono et al. |
| 5,949,530 A | 9/1999 | Wetteborn |
| 5,956,661 A | 9/1999 | Lefebvre et al. |
| 5,956,857 A | 9/1999 | Raab |
| 5,969,321 A | 10/1999 | Danielson et al. |
| 5,973,788 A | 10/1999 | Pettersen et al. |
| 5,978,748 A | 11/1999 | Raab |
| 5,983,936 A | 11/1999 | Schwieterman et al. |
| 5,988,862 A | 11/1999 | Kacyra et al. |
| 5,991,011 A | 11/1999 | Damm |
| 5,996,790 A | 12/1999 | Yamada et al. |
| 5,997,779 A | 12/1999 | Potter |
| 6,040,898 A | 3/2000 | Mrosik et al. |
| D423,534 S | 4/2000 | Raab et al. |
| 6,050,615 A | 4/2000 | Weinhold |
| 6,057,915 A | 5/2000 | Squire et al. |
| 6,060,889 A | 5/2000 | Hocker |
| 6,067,116 A | 5/2000 | Yamano et al. |
| 6,069,700 A | 5/2000 | Rudnick et al. |
| 6,077,306 A | 6/2000 | Metzger et al. |
| 6,112,423 A | 9/2000 | Sheehan |
| 6,115,511 A | 9/2000 | Sakai et al. |

(56) References Cited

U.S. PATENT DOCUMENTS

| | | | |
|---|---|---|---|
| 6,125,337 A | 9/2000 | Rosenberg et al. |
| 6,131,299 A | 10/2000 | Raab et al. |
| 6,134,507 A | 10/2000 | Markey, Jr. et al. |
| 6,138,915 A | 10/2000 | Danielson et al. |
| 6,149,112 A | 11/2000 | Thieltges |
| 6,151,789 A | 11/2000 | Raab et al. |
| 6,163,294 A | 12/2000 | Talbot |
| 6,166,504 A | 12/2000 | Iida et al. |
| 6,166,809 A | 12/2000 | Pettersen et al. |
| 6,166,811 A | 12/2000 | Long et al. |
| 6,204,651 B1 | 3/2001 | Marcus et al. |
| 6,204,961 B1 | 3/2001 | Anderson et al. |
| 6,219,928 B1 | 4/2001 | Raab et al. |
| D441,632 S | 5/2001 | Raab et al. |
| 6,240,651 B1 | 6/2001 | Schroeder et al. |
| 6,253,458 B1 | 7/2001 | Raab et al. |
| 6,282,195 B1 | 8/2001 | Miller et al. |
| 6,285,390 B1 | 9/2001 | Blake |
| 6,298,569 B1 | 10/2001 | Raab et al. |
| 6,339,410 B1 | 1/2002 | Milner et al. |
| 6,349,249 B1 | 2/2002 | Cunningham |
| 6,366,831 B1 | 4/2002 | Raab |
| 6,408,252 B1 | 6/2002 | De Smet |
| 6,418,774 B1 | 7/2002 | Brogaardh et al. |
| 6,438,507 B1 | 8/2002 | Imai |
| 6,438,856 B1 | 8/2002 | Kaczynski |
| 6,442,419 B1 | 8/2002 | Chu et al. |
| 6,445,446 B1 | 9/2002 | Kumagai et al. |
| 6,460,004 B2 | 10/2002 | Greer et al. |
| 6,470,584 B1 | 10/2002 | Stoodley |
| 6,477,784 B2 | 11/2002 | Schroeder et al. |
| 6,480,270 B1 | 11/2002 | Studnicka et al. |
| 6,483,106 B1 | 11/2002 | Ohtomo et al. |
| 6,497,394 B1 | 12/2002 | Dunchock |
| 6,504,602 B1 | 1/2003 | Hinderling |
| 6,512,575 B1 | 1/2003 | Marchi |
| 6,519,860 B1 | 2/2003 | Bieg et al. |
| D472,824 S | 4/2003 | Raab et al. |
| 6,542,249 B1 | 4/2003 | Kofman et al. |
| 6,547,397 B1 | 4/2003 | Kaufman et al. |
| 6,598,306 B2 | 7/2003 | Eaton |
| 6,611,346 B2 | 8/2003 | Granger |
| 6,611,617 B1 | 8/2003 | Crampton |
| D479,544 S | 9/2003 | Raab et al. |
| 6,612,044 B2 | 9/2003 | Raab et al. |
| 6,621,065 B1 | 9/2003 | Fukumoto et al. |
| 6,626,339 B2 | 9/2003 | Gates et al. |
| 6,633,051 B1 | 10/2003 | Holloway et al. |
| 6,649,208 B2 | 11/2003 | Rodgers |
| 6,650,402 B2 | 11/2003 | Sullivan et al. |
| 6,668,466 B1 | 12/2003 | Bieg et al. |
| 6,675,122 B1 | 1/2004 | Markendorf et al. |
| 6,681,495 B2 | 1/2004 | Masayuki et al. |
| 6,710,859 B2 | 3/2004 | Shirai et al. |
| D490,831 S | 6/2004 | Raab et al. |
| D491,210 S | 6/2004 | Raab et al. |
| 6,750,873 B1 | 6/2004 | Bernardini et al. |
| 6,753,876 B2 | 6/2004 | Brooksby et al. |
| 6,759,649 B2 | 7/2004 | Hipp |
| 6,759,979 B2 | 7/2004 | Vashisth et al. |
| 6,764,185 B1 | 7/2004 | Beardsley et al. |
| 6,789,327 B2 | 9/2004 | Roth et al. |
| 6,820,346 B2 | 11/2004 | Raab et al. |
| 6,822,749 B1 | 11/2004 | Christoph |
| 6,825,923 B2 | 11/2004 | Hamar et al. |
| 6,826,664 B2 | 11/2004 | Hocker, III et al. |
| 6,847,436 B2 | 1/2005 | Bridges |
| 6,856,381 B2 | 2/2005 | Christoph |
| 6,858,836 B1 | 2/2005 | Hartrumpf |
| 6,859,269 B2 | 2/2005 | Ohtomo et al. |
| 6,862,097 B2 | 3/2005 | Yanagisawa et al. |
| 6,868,359 B2 | 3/2005 | Raab |
| 6,879,933 B2 | 4/2005 | Steffey et al. |
| 6,889,903 B1 | 5/2005 | Koenck |
| 6,892,465 B2 | 5/2005 | Raab et al. |
| 6,894,767 B2 | 5/2005 | Ishinabe et al. |
| 6,895,347 B2 | 5/2005 | Dorny et al. |
| 6,901,673 B1 | 6/2005 | Cobb et al. |
| 6,904,691 B2 | 6/2005 | Raab et al. |
| 6,914,678 B1 | 7/2005 | Ulrichsen et al. |
| 6,917,415 B2 | 7/2005 | Gogolla et al. |
| 6,920,697 B2 | 7/2005 | Raab et al. |
| 6,922,234 B2 | 7/2005 | Hoffman et al. |
| 6,922,252 B2 * | 7/2005 | Harvill ............... G01B 11/00 356/614 |
| 6,925,722 B2 | 8/2005 | Raab et al. |
| 6,931,745 B2 | 8/2005 | Granger |
| 6,935,036 B2 | 8/2005 | Raab et al. |
| 6,935,748 B2 | 8/2005 | Kaufman et al. |
| 6,948,255 B2 | 9/2005 | Russell |
| 6,957,496 B2 | 10/2005 | Raab et al. |
| 6,965,843 B2 | 11/2005 | Raab et al. |
| 6,973,734 B2 | 12/2005 | Raab et al. |
| 6,988,322 B2 | 1/2006 | Raab et al. |
| 6,989,890 B2 | 1/2006 | Riegl et al. |
| 7,003,892 B2 | 2/2006 | Eaton et al. |
| 7,006,084 B1 | 2/2006 | Buss et al. |
| 7,024,032 B2 | 4/2006 | Kidd et al. |
| 7,029,126 B2 | 4/2006 | Tang |
| 7,032,321 B2 | 4/2006 | Raab et al. |
| 7,040,136 B2 | 5/2006 | Forss et al. |
| 7,051,447 B2 | 5/2006 | Kikuchi et al. |
| 7,069,124 B1 | 6/2006 | Whittaker et al. |
| 7,076,420 B1 | 7/2006 | Snyder et al. |
| 7,106,421 B2 | 9/2006 | Matsuura et al. |
| 7,117,107 B2 | 10/2006 | Dorny et al. |
| 7,120,092 B2 | 10/2006 | Del Prado Pavon et al. |
| 7,127,822 B2 | 10/2006 | Kumagai et al. |
| 7,136,153 B2 | 11/2006 | Mori et al. |
| 7,140,213 B2 | 11/2006 | Feucht et al. |
| 7,142,289 B2 | 11/2006 | Ando et al. |
| 7,145,926 B2 | 12/2006 | Vitruk et al. |
| 7,152,456 B2 | 12/2006 | Eaton |
| 7,174,651 B2 | 2/2007 | Raab et al. |
| 7,180,072 B2 | 2/2007 | Persi et al. |
| 7,184,047 B1 | 2/2007 | Crampton |
| 7,190,465 B2 | 3/2007 | Froehlich et al. |
| 7,191,541 B1 | 3/2007 | Weekers et al. |
| 7,193,690 B2 | 3/2007 | Ossig et al. |
| 7,196,509 B2 | 3/2007 | Teng |
| 7,199,872 B2 | 4/2007 | Van Cranenbroeck |
| 7,200,246 B2 | 4/2007 | Cofer et al. |
| 7,202,941 B2 | 4/2007 | Munro |
| 7,230,689 B2 | 6/2007 | Lau |
| 7,242,590 B1 | 7/2007 | Yeap et al. |
| 7,246,030 B2 | 7/2007 | Raab et al. |
| 7,249,421 B2 | 7/2007 | MacManus et al. |
| 7,256,899 B1 | 8/2007 | Faul et al. |
| 7,269,910 B2 | 9/2007 | Raab et al. |
| D551,943 S | 10/2007 | Hodjat et al. |
| 7,285,793 B2 | 10/2007 | Husted |
| 7,296,364 B2 | 11/2007 | Seitz et al. |
| 7,296,955 B2 | 11/2007 | Dreier |
| 7,296,979 B2 | 11/2007 | Raab et al. |
| 7,306,339 B2 | 12/2007 | Kaufman et al. |
| 7,307,701 B2 | 12/2007 | Hoffman, II |
| 7,312,862 B2 | 12/2007 | Zumbrunn et al. |
| 7,313,264 B2 | 12/2007 | Crampton |
| D559,657 S | 1/2008 | Wohlford et al. |
| 7,319,512 B2 | 1/2008 | Ohtomo et al. |
| 7,330,242 B2 | 2/2008 | Reichert et al. |
| 7,337,344 B2 | 2/2008 | Barman et al. |
| 7,342,650 B2 | 3/2008 | Kern et al. |
| 7,348,822 B2 | 3/2008 | Baer |
| 7,352,446 B2 | 4/2008 | Bridges et al. |
| 7,360,648 B1 | 4/2008 | Blaschke |
| 7,372,558 B2 | 5/2008 | Kaufman et al. |
| 7,372,581 B2 | 5/2008 | Raab et al. |
| 7,383,638 B2 | 6/2008 | Granger |
| 7,388,654 B2 | 6/2008 | Raab et al. |
| 7,389,870 B2 | 6/2008 | Slappay |
| 7,395,606 B2 | 7/2008 | Crampton |
| 7,400,384 B1 | 7/2008 | Evans et al. |
| 7,403,268 B2 | 7/2008 | England et al. |

(56) References Cited

U.S. PATENT DOCUMENTS

| | | | |
|---|---|---|---|
| 7,403,269 B2 * | 7/2008 | Yamashita | G01S 17/42 356/5.01 |
| 7,430,068 B2 | 9/2008 | Becker et al. | |
| 7,430,070 B2 | 9/2008 | Soreide et al. | |
| 7,441,341 B2 | 10/2008 | Eaton | |
| 7,443,555 B2 | 10/2008 | Blug et al. | |
| 7,447,931 B1 | 11/2008 | Rischar et al. | |
| 7,449,876 B2 | 11/2008 | Pleasant et al. | |
| 7,454,265 B2 | 11/2008 | Marsh | |
| 7,463,368 B2 | 12/2008 | Morden et al. | |
| 7,477,359 B2 * | 1/2009 | England | G01S 7/51 356/4.01 |
| 7,477,360 B2 | 1/2009 | England et al. | |
| 7,480,037 B2 | 1/2009 | Palmateer et al. | |
| 2,452,033 A1 | 2/2009 | Born | |
| 7,508,496 B2 | 3/2009 | Mettenleiter et al. | |
| 7,508,971 B2 | 3/2009 | Vaccaro et al. | |
| 7,515,256 B2 | 4/2009 | Ohtomo et al. | |
| 7,525,276 B2 | 4/2009 | Eaton | |
| 7,527,205 B2 | 5/2009 | Zhu et al. | |
| 7,528,768 B2 | 5/2009 | Wakayama et al. | |
| 7,541,830 B2 | 6/2009 | Fahrbach et al. | |
| 7,545,517 B2 | 6/2009 | Rueb et al. | |
| 7,546,689 B2 | 6/2009 | Ferrari et al. | |
| 7,551,771 B2 | 6/2009 | England, III | |
| 7,552,644 B2 | 6/2009 | Haase et al. | |
| 7,557,824 B2 | 7/2009 | Holliman | |
| 7,561,598 B2 | 7/2009 | Stratton et al. | |
| 7,564,250 B2 | 7/2009 | Hocker | |
| 7,568,293 B2 | 8/2009 | Ferrari | |
| 7,578,069 B2 | 8/2009 | Eaton | |
| D599,226 S | 9/2009 | Gerent et al. | |
| 7,589,595 B2 | 9/2009 | Cutler | |
| 7,589,825 B2 | 9/2009 | Orchard et al. | |
| 7,591,077 B2 | 9/2009 | Pettersson | |
| 7,591,078 B2 | 9/2009 | Crampton | |
| 7,599,106 B2 | 10/2009 | Matsumoto et al. | |
| 7,600,061 B2 | 10/2009 | Honda | |
| 7,602,873 B2 | 10/2009 | Eidson | |
| 7,604,207 B2 | 10/2009 | Hasloecher et al. | |
| 7,610,175 B2 | 10/2009 | Eidson | |
| 7,614,157 B2 | 11/2009 | Granger | |
| 7,624,510 B2 | 12/2009 | Ferrari | |
| 7,625,335 B2 | 12/2009 | Deichmann et al. | |
| 7,626,690 B2 | 12/2009 | Kumagai et al. | |
| D607,350 S | 1/2010 | Cooduvalli et al. | |
| 7,656,751 B2 | 2/2010 | Rischar et al. | |
| 7,659,995 B2 | 2/2010 | Knighton et al. | |
| D610,926 S | 3/2010 | Gerent et al. | |
| 7,693,325 B2 | 4/2010 | Pulla et al. | |
| 7,697,748 B2 | 4/2010 | Dimsdale et al. | |
| 7,701,592 B2 | 4/2010 | Saint Clair et al. | |
| 7,712,224 B2 | 5/2010 | Hicks | |
| 7,721,396 B2 | 5/2010 | Fleischman | |
| 7,728,833 B2 | 6/2010 | Verma et al. | |
| 7,728,963 B2 | 6/2010 | Kirschner | |
| 7,733,544 B2 | 6/2010 | Becker et al. | |
| 7,735,234 B2 | 6/2010 | Briggs et al. | |
| 7,743,524 B2 | 6/2010 | Eaton et al. | |
| 7,752,003 B2 | 7/2010 | MacManus | |
| 7,756,615 B2 | 7/2010 | Barfoot et al. | |
| 7,765,707 B2 | 8/2010 | Tomelleri | |
| 7,769,559 B2 | 8/2010 | Reichert | |
| 7,774,949 B2 | 8/2010 | Ferrari | |
| 7,777,761 B2 | 8/2010 | England et al. | |
| 7,779,548 B2 | 8/2010 | Ferrari | |
| 7,779,553 B2 | 8/2010 | Jordil et al. | |
| 7,784,194 B2 | 8/2010 | Raab et al. | |
| 7,787,670 B2 | 8/2010 | Urushiya | |
| 7,793,425 B2 | 9/2010 | Bailey | |
| 7,798,453 B2 | 9/2010 | Maningo et al. | |
| 7,800,758 B1 | 9/2010 | Bridges et al. | |
| 7,804,602 B2 | 9/2010 | Raab | |
| 7,805,851 B2 | 10/2010 | Pettersson | |
| 7,805,854 B2 | 10/2010 | Eaton | |
| 7,809,518 B2 | 10/2010 | Zhu et al. | |
| 7,834,985 B2 | 11/2010 | Morcom | |
| 7,847,922 B2 | 12/2010 | Gittinger et al. | |
| RE42,055 E | 1/2011 | Raab | |
| 7,869,005 B2 | 1/2011 | Ossig et al. | |
| RE42,082 E | 2/2011 | Raab et al. | |
| 7,881,896 B2 | 2/2011 | Atwell et al. | |
| 7,889,324 B2 | 2/2011 | Yamamoto | |
| 7,891,248 B2 | 2/2011 | Hough et al. | |
| 7,900,714 B2 | 3/2011 | Milbourne et al. | |
| 7,903,245 B2 | 3/2011 | Miousset et al. | |
| 7,903,261 B2 | 3/2011 | Saint Clair et al. | |
| 7,908,757 B2 | 3/2011 | Ferrari | |
| 7,933,055 B2 | 4/2011 | Jensen et al. | |
| 7,935,928 B2 | 5/2011 | Serger et al. | |
| 7,965,747 B2 | 6/2011 | Kumano | |
| 7,982,866 B2 | 7/2011 | Vogel | |
| D643,319 S | 8/2011 | Ferrari et al. | |
| 7,990,397 B2 | 8/2011 | Bukowski et al. | |
| 7,994,465 B1 | 8/2011 | Bamji et al. | |
| 7,995,834 B1 | 8/2011 | Knighton et al. | |
| 8,001,697 B2 | 8/2011 | Danielson et al. | |
| 8,020,657 B2 | 9/2011 | Allard et al. | |
| 8,022,812 B2 | 9/2011 | Beniyama et al. | |
| 8,028,432 B2 | 10/2011 | Bailey et al. | |
| 8,036,775 B2 | 10/2011 | Matsumoto et al. | |
| 8,045,762 B2 | 10/2011 | Otani et al. | |
| 8,051,710 B2 | 11/2011 | Van Dam et al. | |
| 8,052,857 B2 | 11/2011 | Townsend | |
| 8,064,046 B2 | 11/2011 | Ossig et al. | |
| 8,065,861 B2 | 11/2011 | Caputo | |
| 8,082,673 B2 | 12/2011 | Desforges et al. | |
| 8,099,877 B2 | 1/2012 | Champ | |
| 8,117,668 B2 | 2/2012 | Crampton et al. | |
| 8,123,350 B2 | 2/2012 | Cannell et al. | |
| 8,152,071 B2 | 4/2012 | Doherty et al. | |
| D659,035 S | 5/2012 | Ferrari et al. | |
| 8,171,650 B2 | 5/2012 | York et al. | |
| 8,179,936 B2 | 5/2012 | Bueche et al. | |
| D662,427 S | 6/2012 | Bailey et al. | |
| 8,218,131 B2 | 7/2012 | Otani et al. | |
| 8,224,032 B2 | 7/2012 | Fuchs et al. | |
| 8,260,483 B2 | 9/2012 | Barfoot et al. | |
| 8,269,984 B2 | 9/2012 | Hinderling et al. | |
| 8,276,286 B2 | 10/2012 | Bailey et al. | |
| 8,284,407 B2 | 10/2012 | Briggs et al. | |
| 8,310,653 B2 | 11/2012 | Ogawa et al. | |
| 8,321,612 B2 | 11/2012 | Hartwich et al. | |
| 8,346,392 B2 | 1/2013 | Walser et al. | |
| 8,346,480 B2 * | 1/2013 | Trepagnier | B60W 30/00 180/167 |
| 8,352,212 B2 | 1/2013 | Fetter et al. | |
| 8,353,059 B2 | 1/2013 | Crampton | |
| D676,341 S | 2/2013 | Bailey et al. | |
| 8,379,191 B2 | 2/2013 | Braunecker et al. | |
| 8,381,704 B2 | 2/2013 | Debelak et al. | |
| 8,384,914 B2 | 2/2013 | Becker et al. | |
| D678,085 S | 3/2013 | Bailey et al. | |
| 8,391,565 B2 | 3/2013 | Purcell et al. | |
| 8,402,669 B2 | 3/2013 | Ferrari et al. | |
| 8,422,035 B2 | 4/2013 | Hinderling et al. | |
| 8,497,901 B2 | 7/2013 | Pettersson | |
| 8,533,967 B2 | 9/2013 | Bailey et al. | |
| 8,537,374 B2 | 9/2013 | Briggs et al. | |
| 8,619,265 B2 * | 12/2013 | Steffey | G01B 11/002 356/614 |
| 8,645,022 B2 | 2/2014 | Yoshimura et al. | |
| 8,659,748 B2 | 2/2014 | Dakin et al. | |
| 8,659,752 B2 | 2/2014 | Cramer et al. | |
| 8,661,700 B2 | 3/2014 | Briggs et al. | |
| 8,677,643 B2 | 3/2014 | Bridges et al. | |
| 8,683,709 B2 | 4/2014 | York | |
| 8,699,007 B2 | 4/2014 | Becker et al. | |
| 8,705,012 B2 | 4/2014 | Greiner et al. | |
| 8,705,016 B2 | 4/2014 | Schumann et al. | |
| 8,718,837 B2 | 5/2014 | Wang et al. | |
| 8,784,425 B2 | 7/2014 | Ritchey et al. | |
| 8,797,552 B2 | 8/2014 | Suzuki et al. | |
| 8,830,485 B2 | 9/2014 | Woloschyn | |

(56) References Cited

U.S. PATENT DOCUMENTS

| | | | |
|---|---|---|---|
| 9,001,312 B2* | 4/2015 | Matsubara | G01S 7/4814 356/5.01 |
| 2001/0004269 A1 | 6/2001 | Shibata et al. | |
| 2002/0032541 A1 | 3/2002 | Raab et al. | |
| 2002/0059042 A1 | 5/2002 | Kacyra et al. | |
| 2002/0087233 A1 | 7/2002 | Raab | |
| 2002/0128790 A1 | 9/2002 | Woodmansee | |
| 2002/0143506 A1 | 10/2002 | D'Aligny et al. | |
| 2002/0149694 A1 | 10/2002 | Seo | |
| 2002/0170192 A1 | 11/2002 | Steffey et al. | |
| 2002/0176097 A1 | 11/2002 | Rodgers | |
| 2003/0002055 A1 | 1/2003 | Kilthau et al. | |
| 2003/0033104 A1 | 2/2003 | Gooche | |
| 2003/0043386 A1 | 3/2003 | Froehlich et al. | |
| 2003/0053037 A1 | 3/2003 | Blaesing-Bangert et al. | |
| 2003/0066954 A1 | 4/2003 | Hipp | |
| 2003/0090646 A1 | 5/2003 | Riegl et al. | |
| 2003/0125901 A1 | 7/2003 | Steffey et al. | |
| 2003/0137449 A1 | 7/2003 | Vashisth et al. | |
| 2003/0142631 A1 | 7/2003 | Silvester | |
| 2003/0167647 A1 | 9/2003 | Raab et al. | |
| 2003/0172536 A1 | 9/2003 | Raab et al. | |
| 2003/0172537 A1 | 9/2003 | Raab et al. | |
| 2003/0179361 A1 | 9/2003 | Ohtomo et al. | |
| 2003/0208919 A1 | 11/2003 | Raab et al. | |
| 2003/0221326 A1 | 12/2003 | Raab et al. | |
| 2004/0004727 A1 | 1/2004 | Yanagisawa et al. | |
| 2004/0022416 A1 | 2/2004 | Lemelson et al. | |
| 2004/0027554 A1 | 2/2004 | Ishinabe et al. | |
| 2004/0040166 A1 | 3/2004 | Raab et al. | |
| 2004/0103547 A1 | 6/2004 | Raab et al. | |
| 2004/0111908 A1 | 6/2004 | Raab et al. | |
| 2004/0119020 A1 | 6/2004 | Bodkin | |
| 2004/0135990 A1 | 7/2004 | Ohtomo et al. | |
| 2004/0139265 A1 | 7/2004 | Hocker, III et al. | |
| 2004/0158355 A1 | 8/2004 | Holmqvist et al. | |
| 2004/0162700 A1 | 8/2004 | Rosenberg et al. | |
| 2004/0179570 A1 | 9/2004 | Vitruk et al. | |
| 2004/0221790 A1 | 11/2004 | Sinclair et al. | |
| 2004/0246462 A1 | 12/2004 | Kaneko et al. | |
| 2004/0246589 A1 | 12/2004 | Kim et al. | |
| 2004/0259533 A1 | 12/2004 | Nixon et al. | |
| 2005/0016008 A1 | 1/2005 | Raab et al. | |
| 2005/0024625 A1 | 2/2005 | Mori et al. | |
| 2005/0028393 A1 | 2/2005 | Raab et al. | |
| 2005/0046823 A1 | 3/2005 | Ando et al. | |
| 2005/0058332 A1 | 3/2005 | Kaufman et al. | |
| 2005/0082262 A1 | 4/2005 | Rueb et al. | |
| 2005/0085940 A1 | 4/2005 | Griggs et al. | |
| 2005/0111514 A1 | 5/2005 | Matsumoto et al. | |
| 2005/0115092 A1 | 6/2005 | Raab et al. | |
| 2005/0141052 A1 | 6/2005 | Becker et al. | |
| 2005/0144799 A1 | 7/2005 | Raab et al. | |
| 2005/0150123 A1 | 7/2005 | Eaton | |
| 2005/0151963 A1 | 7/2005 | Pulla et al. | |
| 2005/0166413 A1 | 8/2005 | Crampton | |
| 2005/0172503 A1 | 8/2005 | Kumagai et al. | |
| 2005/0188557 A1 | 9/2005 | Raab et al. | |
| 2005/0190384 A1 | 9/2005 | Persi et al. | |
| 2005/0259271 A1 | 11/2005 | Christoph | |
| 2005/0276466 A1 | 12/2005 | Vaccaro et al. | |
| 2005/0283989 A1 | 12/2005 | Pettersson | |
| 2006/0016086 A1 | 1/2006 | Raab et al. | |
| 2006/0017720 A1 | 1/2006 | Li | |
| 2006/0026851 A1 | 2/2006 | Raab et al. | |
| 2006/0028203 A1 | 2/2006 | Kawashima et al. | |
| 2006/0053647 A1 | 3/2006 | Raab et al. | |
| 2006/0056459 A1 | 3/2006 | Stratton et al. | |
| 2006/0056559 A1 | 3/2006 | Pleasant et al. | |
| 2006/0059270 A1 | 3/2006 | Pleasant et al. | |
| 2006/0061566 A1 | 3/2006 | Verma et al. | |
| 2006/0066836 A1 | 3/2006 | Bridges et al. | |
| 2006/0088044 A1 | 4/2006 | Hammerl et al. | |
| 2006/0096108 A1 | 5/2006 | Raab et al. | |
| 2006/0103853 A1 | 5/2006 | Palmateer | |
| 2006/0109536 A1 | 5/2006 | Mettenleiter et al. | |
| 2006/0123649 A1 | 6/2006 | Muller | |
| 2006/0129349 A1 | 6/2006 | Raab et al. | |
| 2006/0132803 A1 | 6/2006 | Clair et al. | |
| 2006/0145703 A1 | 7/2006 | Steinbichler et al. | |
| 2006/0169050 A1 | 8/2006 | Kobayashi et al. | |
| 2006/0169608 A1 | 8/2006 | Carnevali et al. | |
| 2006/0170870 A1 | 8/2006 | Kaufman et al. | |
| 2006/0182314 A1 | 8/2006 | England et al. | |
| 2006/0186301 A1 | 8/2006 | Dozier et al. | |
| 2006/0193521 A1 | 8/2006 | England, III et al. | |
| 2006/0241791 A1 | 10/2006 | Pokorny et al. | |
| 2006/0244746 A1 | 11/2006 | England et al. | |
| 2006/0245717 A1 | 11/2006 | Ossig et al. | |
| 2006/0279246 A1 | 12/2006 | Hashimoto et al. | |
| 2006/0282574 A1 | 12/2006 | Zotov et al. | |
| 2006/0287769 A1 | 12/2006 | Yanagita et al. | |
| 2006/0291970 A1 | 12/2006 | Granger | |
| 2007/0019212 A1 | 1/2007 | Gatsios et al. | |
| 2007/0030841 A1 | 2/2007 | Lee et al. | |
| 2007/0043526 A1 | 2/2007 | De Jonge et al. | |
| 2007/0050774 A1 | 3/2007 | Eldson et al. | |
| 2007/0055806 A1 | 3/2007 | Stratton et al. | |
| 2007/0058154 A1 | 3/2007 | Reichert et al. | |
| 2007/0058162 A1 | 3/2007 | Granger | |
| 2007/0064976 A1 | 3/2007 | England, III | |
| 2007/0097382 A1 | 5/2007 | Granger | |
| 2007/0100498 A1 | 5/2007 | Matsumoto et al. | |
| 2007/0105238 A1 | 5/2007 | Mandl et al. | |
| 2007/0118269 A1 | 5/2007 | Gibson et al. | |
| 2007/0122250 A1 | 5/2007 | Mullner | |
| 2007/0142970 A1 | 6/2007 | Burbank et al. | |
| 2007/0147265 A1 | 6/2007 | Eidson et al. | |
| 2007/0147435 A1 | 6/2007 | Hamilton et al. | |
| 2007/0147562 A1 | 6/2007 | Eidson | |
| 2007/0150111 A1 | 6/2007 | Wu et al. | |
| 2007/0151390 A1 | 7/2007 | Blumenkranz et al. | |
| 2007/0153297 A1 | 7/2007 | Lau | |
| 2007/0163134 A1 | 7/2007 | Eaton | |
| 2007/0163136 A1 | 7/2007 | Eaton et al. | |
| 2007/0171394 A1 | 7/2007 | Steiner et al. | |
| 2007/0176648 A1 | 8/2007 | Baer | |
| 2007/0177016 A1 | 8/2007 | Wu | |
| 2007/0181685 A1 | 8/2007 | Zhu et al. | |
| 2007/0183459 A1 | 8/2007 | Eidson | |
| 2007/0185682 A1 | 8/2007 | Eidson | |
| 2007/0217169 A1 | 9/2007 | Yeap et al. | |
| 2007/0217170 A1 | 9/2007 | Yeap et al. | |
| 2007/0221522 A1 | 9/2007 | Yamada et al. | |
| 2007/0223477 A1 | 9/2007 | Eidson | |
| 2007/0229801 A1 | 10/2007 | Tearney et al. | |
| 2007/0229929 A1 | 10/2007 | Soreide et al. | |
| 2007/0247615 A1 | 10/2007 | Bridges et al. | |
| 2007/0248122 A1 | 10/2007 | Hamilton | |
| 2007/0256311 A1 | 11/2007 | Ferrari | |
| 2007/0257660 A1 | 11/2007 | Pleasant et al. | |
| 2007/0258378 A1 | 11/2007 | Hamilton | |
| 2007/0282564 A1 | 12/2007 | Sprague et al. | |
| 2007/0294045 A1 | 12/2007 | Atwell et al. | |
| 2008/0046221 A1 | 2/2008 | Stathis | |
| 2008/0052808 A1 | 3/2008 | Leick et al. | |
| 2008/0052936 A1 | 3/2008 | Briggs et al. | |
| 2008/0066583 A1 | 3/2008 | Lott et al. | |
| 2008/0068103 A1 | 3/2008 | Cutler | |
| 2008/0075325 A1 | 3/2008 | Otani et al. | |
| 2008/0075326 A1* | 3/2008 | Otani | G01C 3/00 382/106 |
| 2008/0080562 A1 | 4/2008 | Burch et al. | |
| 2008/0096108 A1 | 4/2008 | Sumiyama et al. | |
| 2008/0098272 A1 | 4/2008 | Fairbanks et al. | |
| 2008/0148585 A1 | 6/2008 | Raab et al. | |
| 2008/0154538 A1 | 6/2008 | Stathis | |
| 2008/0179206 A1 | 7/2008 | Feinstein et al. | |
| 2008/0183065 A1 | 7/2008 | Goldbach | |
| 2008/0196260 A1 | 8/2008 | Pettersson | |
| 2008/0204699 A1 | 8/2008 | Benz et al. | |
| 2008/0216552 A1 | 9/2008 | Ibach et al. | |
| 2008/0218728 A1 | 9/2008 | Kirschner | |
| 2008/0228331 A1 | 9/2008 | McNerney et al. | |

(56) References Cited

U.S. PATENT DOCUMENTS

| | | |
|---|---|---|
| 2008/0232269 A1 | 9/2008 | Tatman et al. |
| 2008/0235969 A1 | 10/2008 | Jordil et al. |
| 2008/0235970 A1 | 10/2008 | Crampton |
| 2008/0240321 A1 | 10/2008 | Narus et al. |
| 2008/0245452 A1 | 10/2008 | Law et al. |
| 2008/0246943 A1 | 10/2008 | Kaufman et al. |
| 2008/0252671 A1 | 10/2008 | Cannell et al. |
| 2008/0256814 A1 | 10/2008 | Pettersson |
| 2008/0257023 A1 | 10/2008 | Jordil et al. |
| 2008/0263411 A1 | 10/2008 | Baney et al. |
| 2008/0271332 A1 | 11/2008 | Jordil et al. |
| 2008/0273758 A1 | 11/2008 | Fuchs et al. |
| 2008/0282564 A1 | 11/2008 | Pettersson |
| 2008/0295349 A1 | 12/2008 | Uhl et al. |
| 2008/0298254 A1 | 12/2008 | Eidson |
| 2008/0302200 A1 | 12/2008 | Tobey |
| 2008/0309460 A1 | 12/2008 | Jefferson et al. |
| 2008/0309546 A1 | 12/2008 | Wakayama et al. |
| 2009/0000136 A1 | 1/2009 | Crampton |
| 2009/0010740 A1 | 1/2009 | Ferrari et al. |
| 2009/0013548 A1 | 1/2009 | Ferrari |
| 2009/0016475 A1 | 1/2009 | Rischar et al. |
| 2009/0021351 A1 | 1/2009 | Beniyama et al. |
| 2009/0031575 A1 | 2/2009 | Tomelleri |
| 2009/0046140 A1 | 2/2009 | Lashmet et al. |
| 2009/0046752 A1 | 2/2009 | Bueche et al. |
| 2009/0046895 A1 | 2/2009 | Pettersson et al. |
| 2009/0049704 A1 | 2/2009 | Styles et al. |
| 2009/0051938 A1 | 2/2009 | Miousset et al. |
| 2009/0083985 A1 | 4/2009 | Ferrari |
| 2009/0089004 A1 | 4/2009 | Vook et al. |
| 2009/0089078 A1 | 4/2009 | Bursey |
| 2009/0089233 A1 | 4/2009 | Gach et al. |
| 2009/0089623 A1 | 4/2009 | Neering et al. |
| 2009/0095047 A1 | 4/2009 | Patel et al. |
| 2009/0100949 A1 | 4/2009 | Shirai et al. |
| 2009/0109797 A1 | 4/2009 | Eidson |
| 2009/0113183 A1 | 4/2009 | Barford et al. |
| 2009/0113229 A1 | 4/2009 | Cataldo et al. |
| 2009/0122805 A1 | 5/2009 | Epps et al. |
| 2009/0125196 A1 | 5/2009 | Velazquez et al. |
| 2009/0133276 A1 | 5/2009 | Bailey et al. |
| 2009/0133494 A1 | 5/2009 | Van Dam et al. |
| 2009/0139105 A1 | 6/2009 | Granger |
| 2009/0157419 A1 | 6/2009 | Bursey |
| 2009/0161091 A1 | 6/2009 | Yamamoto |
| 2009/0165317 A1 | 7/2009 | Little |
| 2009/0177435 A1 | 7/2009 | Heininen |
| 2009/0177438 A1 | 7/2009 | Raab |
| 2009/0185741 A1 | 7/2009 | Nahari et al. |
| 2009/0187373 A1 | 7/2009 | Atwell |
| 2009/0241360 A1 | 10/2009 | Tait et al. |
| 2009/0249634 A1 | 10/2009 | Pettersson |
| 2009/0265946 A1 | 10/2009 | Jordil et al. |
| 2009/0273771 A1 | 11/2009 | Gittinger et al. |
| 2009/0299689 A1 | 12/2009 | Stubben et al. |
| 2009/0322859 A1 | 12/2009 | Shelton et al. |
| 2009/0323121 A1 | 12/2009 | Valkenburg et al. |
| 2009/0323742 A1 | 12/2009 | Kumano |
| 2010/0030421 A1 | 2/2010 | Yoshimura et al. |
| 2010/0040742 A1 | 2/2010 | Dijkhuis et al. |
| 2010/0049891 A1 | 2/2010 | Hartwich et al. |
| 2010/0057392 A1 | 3/2010 | York |
| 2010/0078866 A1 | 4/2010 | Pettersson |
| 2010/0095542 A1 | 4/2010 | Ferrari |
| 2010/0122920 A1 | 5/2010 | Butter et al. |
| 2010/0123892 A1 | 5/2010 | Miller et al. |
| 2010/0134596 A1 | 6/2010 | Becker |
| 2010/0135534 A1 | 6/2010 | Weston et al. |
| 2010/0148013 A1 | 6/2010 | Bhotika et al. |
| 2010/0195086 A1 | 8/2010 | Ossig et al. |
| 2010/0207938 A1 | 8/2010 | Yau et al. |
| 2010/0208062 A1 | 8/2010 | Pettersson |
| 2010/0208318 A1 | 8/2010 | Jensen et al. |
| 2010/0245851 A1 | 9/2010 | Teodorescu |
| 2010/0277747 A1 | 11/2010 | Rueb et al. |
| 2010/0281705 A1 | 11/2010 | Verdi et al. |
| 2010/0286941 A1 | 11/2010 | Merlot |
| 2010/0312524 A1 | 12/2010 | Siercks et al. |
| 2010/0318319 A1 | 12/2010 | Maierhofer |
| 2010/0321152 A1 | 12/2010 | Argudyaev et al. |
| 2010/0325907 A1 | 12/2010 | Tait |
| 2011/0000095 A1 | 1/2011 | Carlson |
| 2011/0001958 A1 | 1/2011 | Bridges et al. |
| 2011/0007305 A1 | 1/2011 | Bridges et al. |
| 2011/0007326 A1 | 1/2011 | Daxauer et al. |
| 2011/0013199 A1 | 1/2011 | Siercks et al. |
| 2011/0019155 A1 | 1/2011 | Daniel et al. |
| 2011/0023578 A1 | 2/2011 | Grasser |
| 2011/0025905 A1 | 2/2011 | Tanaka |
| 2011/0043515 A1 | 2/2011 | Stathis |
| 2011/0066781 A1 | 3/2011 | Debelak et al. |
| 2011/0094908 A1 | 4/2011 | Trieu et al. |
| 2011/0107611 A1 | 5/2011 | Desforges et al. |
| 2011/0107612 A1 | 5/2011 | Ferrari et al. |
| 2011/0107613 A1 | 5/2011 | Tait |
| 2011/0107614 A1 | 5/2011 | Champ |
| 2011/0111849 A1 | 5/2011 | Sprague et al. |
| 2011/0112786 A1 | 5/2011 | Desforges et al. |
| 2011/0119025 A1 | 5/2011 | Fetter et al. |
| 2011/0123097 A1 | 5/2011 | Van Coppenolle et al. |
| 2011/0164114 A1 | 7/2011 | Kobayashi et al. |
| 2011/0166824 A1 | 7/2011 | Haisty et al. |
| 2011/0169924 A1 | 7/2011 | Haisty et al. |
| 2011/0173823 A1 | 7/2011 | Bailey et al. |
| 2011/0173827 A1 | 7/2011 | Bailey et al. |
| 2011/0173828 A1 | 7/2011 | York |
| 2011/0178755 A1 | 7/2011 | York |
| 2011/0178758 A1 | 7/2011 | Atwell et al. |
| 2011/0178762 A1 | 7/2011 | York |
| 2011/0178764 A1 | 7/2011 | York |
| 2011/0178765 A1 | 7/2011 | Atwell et al. |
| 2011/0192043 A1 | 8/2011 | Ferrari et al. |
| 2011/0273568 A1 | 11/2011 | Lagassey et al. |
| 2011/0282622 A1 | 11/2011 | Canter et al. |
| 2011/0288684 A1 | 11/2011 | Farlow et al. |
| 2012/0019806 A1 | 1/2012 | Becker et al. |
| 2012/0033069 A1 | 2/2012 | Becker et al. |
| 2012/0035788 A1 | 2/2012 | Trepagnier et al. |
| 2012/0035798 A1 | 2/2012 | Barfoot et al. |
| 2012/0044476 A1 | 2/2012 | Earhart et al. |
| 2012/0046820 A1 | 2/2012 | Allard et al. |
| 2012/0069325 A1 | 3/2012 | Schumann et al. |
| 2012/0069352 A1 | 3/2012 | Ossig et al. |
| 2012/0070077 A1 | 3/2012 | Ossig et al. |
| 2012/0113913 A1 | 5/2012 | Tiirola et al. |
| 2012/0140083 A1 | 6/2012 | Schultz et al. |
| 2012/0140244 A1 | 6/2012 | Gittinger et al. |
| 2012/0154786 A1 | 6/2012 | Gosch et al. |
| 2012/0155744 A1 | 6/2012 | Kennedy et al. |
| 2012/0169876 A1 | 7/2012 | Reichert et al. |
| 2012/0181194 A1 | 7/2012 | McEwan et al. |
| 2012/0197439 A1 | 8/2012 | Wang et al. |
| 2012/0210678 A1 | 8/2012 | Alcouloumre et al. |
| 2012/0217357 A1 | 8/2012 | Franke |
| 2012/0229788 A1 | 9/2012 | Schumann et al. |
| 2012/0260512 A1 | 10/2012 | Kretschmer et al. |
| 2012/0260611 A1 | 10/2012 | Jones et al. |
| 2012/0262700 A1 | 10/2012 | Schumann et al. |
| 2012/0287265 A1 | 11/2012 | Schumann et al. |
| 2013/0010307 A1 | 1/2013 | Greiner et al. |
| 2013/0025143 A1 | 1/2013 | Bailey et al. |
| 2013/0025144 A1 | 1/2013 | Briggs et al. |
| 2013/0027515 A1 | 1/2013 | Vinther et al. |
| 2013/0062243 A1 | 3/2013 | Chang et al. |
| 2013/0070250 A1 | 3/2013 | Ditte et al. |
| 2013/0094024 A1 | 4/2013 | Ruhland et al. |
| 2013/0097882 A1 | 4/2013 | Bridges et al. |
| 2013/0125408 A1 | 5/2013 | Atwell et al. |
| 2013/0162472 A1 | 6/2013 | Najim et al. |
| 2013/0176453 A1 | 7/2013 | Mate et al. |
| 2013/0201487 A1 | 8/2013 | Ossig et al. |
| 2013/0205606 A1 | 8/2013 | Briggs et al. |
| 2013/0212889 A9 | 8/2013 | Bridges et al. |

(56) References Cited

U.S. PATENT DOCUMENTS

| | | |
|---|---|---|
| 2013/0222816 A1 | 8/2013 | Briggs et al. |
| 2013/0300740 A1 | 11/2013 | Snyder et al. |
| 2014/0002608 A1 | 1/2014 | Atwell et al. |
| 2014/0049784 A1 | 2/2014 | Woloschyn et al. |
| 2014/0063489 A1 | 3/2014 | Steffey et al. |
| 2014/0078519 A1 | 3/2014 | Steffey et al. |
| 2014/0226190 A1 | 8/2014 | Bridges et al. |
| 2014/0240690 A1 | 8/2014 | Newman et al. |
| 2014/0300906 A1 | 10/2014 | Becker et al. |
| 2014/0362424 A1 | 12/2014 | Bridges et al. |
| 2015/0085068 A1 | 3/2015 | Becker et al. |
| 2015/0085301 A1 | 3/2015 | Becker et al. |
| 2015/0160342 A1 | 6/2015 | Zweigle et al. |

FOREIGN PATENT DOCUMENTS

| | | |
|---|---|---|
| CN | 2236119 y | 9/1996 |
| CN | 1307241 A | 8/2001 |
| CN | 2508896 Y | 9/2002 |
| CN | 2665668 Y | 12/2004 |
| CN | 1630804 A | 6/2005 |
| CN | 1630805 A | 6/2005 |
| CN | 1688867 A | 10/2005 |
| CN | 1735789 | 2/2006 |
| CN | 1812868 A | 8/2006 |
| CN | 1818537 A | 8/2006 |
| CN | 1838102 A | 9/2006 |
| CN | 1839293 A | 9/2006 |
| CN | 1853084 A | 10/2006 |
| CN | 1926400 | 3/2007 |
| CN | 101024286 A | 8/2007 |
| CN | 101156043 A | 4/2008 |
| CN | 101163939 A | 4/2008 |
| CN | 101371099 A | 2/2009 |
| CN | 101416024 | 4/2009 |
| CN | 101484828 | 7/2009 |
| CN | 201266071 Y | 7/2009 |
| CN | 101506684 | 8/2009 |
| CN | 101511529 A | 8/2009 |
| DE | 2216765 A1 | 4/1972 |
| DE | 3227980 A1 | 5/1983 |
| DE | 3245060 A1 | 7/1983 |
| DE | 3340317 A1 | 8/1984 |
| DE | 4027990 C1 | 2/1992 |
| DE | 4222642 A1 | 1/1994 |
| DE | 4340756 A1 | 6/1994 |
| DE | 4303804 A1 | 8/1994 |
| DE | 4445464 A1 | 7/1995 |
| DE | 4410775 A1 | 10/1995 |
| DE | 4412044 A1 | 10/1995 |
| DE | 29622033 | 2/1997 |
| DE | 19543763 A1 | 5/1997 |
| DE | 19601875 A1 | 7/1997 |
| DE | 19607345 A1 | 8/1997 |
| DE | 19720049 A1 | 11/1998 |
| DE | 19811550 A1 | 9/1999 |
| DE | 19820307 A1 | 11/1999 |
| DE | 19850118 A1 | 5/2000 |
| DE | 19928958 A1 | 11/2000 |
| DE | 10026357 A1 | 1/2002 |
| DE | 20208077 A1 | 5/2002 |
| DE | 10137241 A1 | 9/2002 |
| DE | 10155488 A1 | 5/2003 |
| DE | 10219054 A1 | 11/2003 |
| DE | 10232028 | 2/2004 |
| DE | 10336458 A1 | 2/2004 |
| DE | 10244643 A1 | 4/2004 |
| DE | 20320216 U1 | 4/2004 |
| DE | 10304188 A1 | 8/2004 |
| DE | 10326848 A1 | 1/2005 |
| DE | 202005000983 U1 | 3/2005 |
| DE | 10361870 A | 7/2005 |
| DE | 102004015668 B3 | 9/2005 |
| DE | 102004015111 A1 | 10/2005 |
| DE | 102004028090 A1 | 12/2005 |
| DE | 10114126 B4 | 8/2006 |
| DE | 202006005643 U1 | 8/2006 |
| DE | 102004010083 B4 | 11/2006 |
| DE | 102005043931 A1 | 3/2007 |
| DE | 102005056265 A1 | 5/2007 |
| DE | 102006053611 A1 | 5/2007 |
| DE | 102005060967 A1 | 6/2007 |
| DE | 102006023902 | 11/2007 |
| DE | 102006024534 A1 | 11/2007 |
| DE | 102006035292 A1 | 1/2008 |
| DE | 202006020299 U1 | 5/2008 |
| DE | 102007037162 A1 | 2/2009 |
| DE | 102008014274 A1 | 8/2009 |
| DE | 102008039838 A1 | 3/2010 |
| DE | 102005036929 B4 | 6/2010 |
| DE | 102008062763 B3 | 7/2010 |
| DE | 102009001894 A1 | 9/2010 |
| DE | 102009035336 B3 | 11/2010 |
| DE | 102009055988 | 3/2011 |
| DE | 102010032723 B3 | 11/2011 |
| DE | 102010032726 B3 | 11/2011 |
| DE | 102010033561 B3 | 12/2011 |
| DE | 102010032725 A1 | 1/2012 |
| DE | 202011051975 U1 | 2/2013 |
| DE | 102012107544 B3 | 5/2013 |
| DE | 102012109481 A1 | 4/2014 |
| EP | 0546784 A2 | 6/1993 |
| EP | 0667549 A2 | 8/1995 |
| EP | 0727642 A1 | 8/1996 |
| EP | 0730210 A1 | 9/1996 |
| EP | 0614517 | 3/1997 |
| EP | 0838696 A1 | 4/1998 |
| EP | 0949524 A1 | 10/1999 |
| EP | 1160539 | 12/2001 |
| EP | 1189124 A1 | 3/2002 |
| EP | 0767357 B1 | 5/2002 |
| EP | 1310764 A2 | 5/2003 |
| EP | 1342989 A2 | 9/2003 |
| EP | 1347267 A1 | 9/2003 |
| EP | 1361414 A1 | 11/2003 |
| EP | 1452279 | 9/2004 |
| EP | 1468791 A1 | 10/2004 |
| EP | 1056987 B1 | 4/2005 |
| EP | 1528410 A1 | 5/2005 |
| EP | 1669713 A1 | 6/2006 |
| EP | 1734425 A2 | 12/2006 |
| EP | 1429109 | 4/2007 |
| EP | 1764579 | 12/2007 |
| EP | 1878543 A2 | 1/2008 |
| EP | 1967930 A2 | 9/2008 |
| EP | 2003419 A1 | 12/2008 |
| EP | 2023077 A1 | 2/2009 |
| EP | 2042905 | 4/2009 |
| EP | 2060530 A1 | 5/2009 |
| EP | 2068067 A1 | 6/2009 |
| EP | 2068114 | 6/2009 |
| EP | 2108917 A1 | 10/2009 |
| EP | 2177868 A2 | 4/2010 |
| EP | 2259013 A1 | 12/2010 |
| EP | 2400261 A1 | 12/2011 |
| FR | 2603228 A1 | 3/1988 |
| FR | 2935043 A1 | 2/2010 |
| GB | 894320 | 4/1962 |
| GB | 1112941 | 5/1968 |
| GB | 2222695 A | 3/1990 |
| GB | 2255648 A | 11/1992 |
| GB | 2336493 A | 10/1999 |
| GB | 2341203 A | 3/2000 |
| GB | 2388661 A | 11/2003 |
| GB | 2420241 A | 5/2006 |
| GB | 2447258 A | 9/2008 |
| GB | 2452033 A | 2/2009 |
| JP | 5581525 | 6/1955 |
| JP | 575584 A | 1/1982 |
| JP | 58171291 | 1/1983 |
| JP | 5827264 | 2/1983 |
| JP | S58-171291 A | 10/1983 |
| JP | 59133890 A | 8/1984 |

(56) References Cited

FOREIGN PATENT DOCUMENTS

| | | |
|---|---|---|
| JP | 61062885 | 3/1986 |
| JP | S61-157095 A | 7/1986 |
| JP | 63135814 A | 6/1988 |
| JP | 0357911 A | 3/1991 |
| JP | 04115108 A | 4/1992 |
| JP | 04225188 | 8/1992 |
| JP | 04267214 A | 9/1992 |
| JP | 0572477 A | 3/1993 |
| JP | 06313710 | 11/1994 |
| JP | 1994313710 A | 11/1994 |
| JP | 06331733 | 12/1994 |
| JP | 06341838 | 12/1994 |
| JP | 074950 A | 1/1995 |
| JP | 07128051 A | 5/1995 |
| JP | 7210586 A | 8/1995 |
| JP | 07229963 A | 8/1995 |
| JP | 0815413 A | 1/1996 |
| JP | 0821714 A | 1/1996 |
| JP | 08129145 A | 5/1996 |
| JP | 08136849 A | 5/1996 |
| JP | 08262140 A | 10/1996 |
| JP | 09021868 | 1/1997 |
| JP | 10213661 A | 8/1998 |
| JP | 1123993 A | 1/1999 |
| JP | 2001056275 | 8/1999 |
| JP | 2000121724 A | 4/2000 |
| JP | 2000249546 A | 9/2000 |
| JP | 2000339468 A | 12/2000 |
| JP | 2001013001 A | 1/2001 |
| JP | 2001021303 A | 1/2001 |
| JP | 2011066211 A | 3/2001 |
| JP | 2001337278 A | 12/2001 |
| JP | 2003050128 A | 2/2003 |
| JP | 2003156330 | 5/2003 |
| JP | 2003156562 A | 5/2003 |
| JP | 2003194526 | 7/2003 |
| JP | 2003202215 A | 7/2003 |
| JP | 2003216255 A | 7/2003 |
| JP | 2003308205 A | 10/2003 |
| JP | 2004109106 A | 4/2004 |
| JP | 2004245832 A | 9/2004 |
| JP | 2004257927 A | 9/2004 |
| JP | 2004333398 A | 11/2004 |
| JP | 2004348575 A | 12/2004 |
| JP | 2005030937 A | 2/2005 |
| JP | 2005055226 A | 3/2005 |
| JP | 2005069700 A | 3/2005 |
| JP | 2005174887 A | 6/2005 |
| JP | 2005517908 | 6/2005 |
| JP | 2005215917 A | 8/2005 |
| JP | 2005221336 A | 8/2005 |
| JP | 2005257510 A | 9/2005 |
| JP | 2006038683 A | 2/2006 |
| JP | 2006102176 A | 4/2006 |
| JP | 2006203404 A | 8/2006 |
| JP | 2006226948 A | 8/2006 |
| JP | 2006241833 A | 9/2006 |
| JP | 2006266821 A | 10/2006 |
| JP | 2006301991 A | 11/2006 |
| JP | 2007514943 A | 6/2007 |
| JP | 2007178943 A | 7/2007 |
| JP | 2008076303 A | 4/2008 |
| JP | 2008082707 A | 4/2008 |
| JP | 2008096123 A | 4/2008 |
| JP | 2008107286 A | 5/2008 |
| JP | 2008304220 A | 12/2008 |
| JP | 2009063339 A | 3/2009 |
| JP | 2009524057 | 6/2009 |
| JP | 2009531674 A | 9/2009 |
| JP | 2009229255 A | 10/2009 |
| JP | 2009541758 A | 11/2009 |
| JP | 2010169405 A | 8/2010 |
| JP | 2013516928 A | 5/2013 |
| JP | 2013517508 A | 5/2013 |
| JP | 2013117417 A | 6/2013 |
| JP | 2013543970 A | 12/2013 |
| WO | 8801924 A1 | 3/1988 |
| WO | 8905512 | 6/1989 |
| WO | 9208568 A1 | 5/1992 |
| WO | 9711399 | 3/1997 |
| WO | 9808050 | 2/1998 |
| WO | 9910706 A1 | 3/1999 |
| WO | 0014474 A1 | 3/2000 |
| WO | 0020880 A2 | 4/2000 |
| WO | 0026612 A1 | 5/2000 |
| WO | 0033149 | 6/2000 |
| WO | 0034733 | 6/2000 |
| WO | 0063645 A1 | 10/2000 |
| WO | 0063681 A2 | 10/2000 |
| WO | 0177613 A1 | 10/2001 |
| WO | 02084327 A2 | 10/2002 |
| WO | 02101323 A2 | 12/2002 |
| WO | 2004096502 A1 | 11/2004 |
| WO | 2005008271 A2 | 1/2005 |
| WO | 2005059473 A2 | 6/2005 |
| WO | 2005072917 A1 | 8/2005 |
| WO | 2005075875 | 8/2005 |
| WO | 2005100908 A1 | 10/2005 |
| WO | 2006000552 A1 | 1/2006 |
| WO | 2006014445 A1 | 2/2006 |
| WO | 2006051264 A1 | 5/2006 |
| WO | 2006053837 A1 | 5/2006 |
| WO | 2007002319 A1 | 1/2007 |
| WO | 2007012198 A1 | 2/2007 |
| WO | 2007028941 A1 | 3/2007 |
| WO | 2007051972 A1 | 5/2007 |
| WO | 2007087198 A1 | 8/2007 |
| WO | 2007118478 A1 | 10/2007 |
| WO | 2007125081 A1 | 11/2007 |
| WO | 2007144906 A1 | 12/2007 |
| WO | 2008019856 A1 | 2/2008 |
| WO | 2008027588 A2 | 3/2008 |
| WO | 2008047171 | 4/2008 |
| WO | 2008048424 A2 | 4/2008 |
| WO | 2008052348 A1 | 5/2008 |
| WO | 2008064276 A3 | 5/2008 |
| WO | 2008066896 A2 | 6/2008 |
| WO | 2008068791 A1 | 6/2008 |
| WO | 2008075170 A1 | 6/2008 |
| WO | 2008121073 A1 | 10/2008 |
| WO | 2008157061 A1 | 12/2008 |
| WO | 2009001165 A1 | 12/2008 |
| WO | 2009016185 A1 | 2/2009 |
| WO | 2009053085 A1 | 4/2009 |
| WO | 2009083452 A1 | 7/2009 |
| WO | 2009095384 A2 | 8/2009 |
| WO | 2009123278 A1 | 10/2009 |
| WO | 2009127526 A1 | 10/2009 |
| WO | 2009130169 A1 | 10/2009 |
| WO | 2009149740 A1 | 12/2009 |
| WO | 2010040742 A1 | 4/2010 |
| WO | 2010092131 A1 | 8/2010 |
| WO | 2010108089 A2 | 9/2010 |
| WO | 2010108644 A2 | 9/2010 |
| WO | 2010148525 A1 | 12/2010 |
| WO | 2011000435 A1 | 1/2011 |
| WO | 2011000955 A1 | 1/2011 |
| WO | 2011021103 A1 | 2/2011 |
| WO | 2011029140 A1 | 3/2011 |
| WO | 2011057130 A2 | 5/2011 |
| WO | 2011060899 A1 | 5/2011 |
| WO | 2011002908 A1 | 6/2011 |
| WO | 2011090829 A2 | 7/2011 |
| WO | 2011090895 A1 | 7/2011 |
| WO | 2012037157 A2 | 3/2012 |
| WO | 2012038446 A1 | 3/2012 |
| WO | 2012061122 A1 | 5/2012 |
| WO | 2012013525 A2 | 8/2012 |
| WO | 2012103525 A2 | 8/2012 |
| WO | 2012112683 A2 | 8/2012 |
| WO | 2012125671 A1 | 9/2012 |
| WO | 2013112455 A1 | 8/2013 |

(56) References Cited

FOREIGN PATENT DOCUMENTS

| WO | 2013188026 A1 | 12/2013 |
|---|---|---|
| WO | 2013190031 A1 | 12/2013 |
| WO | 2014128498 A2 | 8/2014 |

OTHER PUBLICATIONS

Leica TPS800 Performance Series—Equipment List, 2004.
Merriam-Webster (m-w.com), "Traverse". 2012. http://www.merriam-webster.com/dictionary/traverse.
MG Lee; "Compact 3D LIDAR based on optically coupled horizontal and vertical Scanning mechanism for the autonomous navigation of robots" (13 pages) vol. 8037; downloaded from http://proceedings.spiedigitallibrary.org/ on Jul. 2, 2013.
MicroScan 3D User Guide, RSI GmbH, 3D Systems & Software, Oberursel, Germany, email: info@rsi-gmbh.de, Copyright RSI Roland Seifert Imaging GmbH 2008.
MOOG Components Group; "Fiber Optic Rotary Joints; Product Guide" (4 pages) Dec. 2010; MOOG, Inc. 2010.
P Ben-Tzvi, et al "Extraction of 3D Images Using Pitch-Actuated 2D Laser Range Finder for Robotic Vision" (6 pages) BNSDOCID <XP 31840390A_1_>.
Provision of the minutes in accordance with Rule 124(4) EPC dated Aug. 14, 2013, filed in Opposition re Application No. 07 785 873.6/ Patent No. 2 062 069, Proprietor: Faro Technologies, Inc., filed by Leica Geosystem AG on Feb. 5, 2013.
Romer "Romer Absolute Arm Maximum Performance Portable Measurement" (Printed 2010); Hexagon Metrology, Inc., http://us:Romer.com; 2010.
Romer "Romer Absolute Arm Product Brochure" (2010); Hexagon Metrology; www.hexagonmetrology.com; Hexagon AB 2010.
RW Boyd "Radiometry and the Detection of Otpical Radiation" (pp. 20-23) 1983 Jon wiley & Sons, Inc.
Sauter, et al., Towards New Hybrid Networks for Industrial Automation, IEEE, 2009.
Se, et al., "Instant Scene Modeler for Crime Scene Reconstruction", MDA, Space Missions, Ontario, Canada, Copyright 2005, IEEE.
Surman et al. "An autonomous mobile robot with a 3D laser range finder for 3D exploration and digitalization of indoor enviornments." Robotics and Autonomous Systems vol. 45 No. 3-4, Dec. 31, 2003, pp. 181-198. Amsterdamn, Netherlands.
The Scene, Journal of the Association for Crime Scene Reconstruction, Apr.-Jun. 2006, vol. 12, Issue 2.
Umeda, K., et al., Registration of Range and Color Images Using Gradient Constraints and Ran Intensity Images, Proceedings of the 17th International Conference onPatern Recognition (ICPR'04), Copyright 2010 IEEE. [Retrieved online Jan. 28, 2010—IEEE.
Williams, J.A., et al., Evaluation of a Novel Multiple Point Set Registration Algorithm, Copyright 2000, [Retrieved on Jan. 18, 2010 at 04:10 from IEEE Xplore].
Yk Cho, et al. "Light-weight 3D LADAR System for Construction Robotic Operations" (pp. 237-244); 26th International Symposium on Automation and Robotics in Construction (ISARC 2009).
Davidson, A. et al., "MonoSLAM: Real-Time Single Camera SLAM", IEEE Transactions on Pattern Analysis and Machine Intelligence, vol. 29, No. 6, Jun. 1, 2007, pp. 1052-1067, XP011179664.
Gebre, Biruk A., et al., "Remotely Operated and Autonomous Mapping System (ROAMS)", Technologies for Practical Robot Applications, TEPRA 2009, IEEE International Conference on Nov. 9, 2009, pp. 173-178, XP031570394.
Harrison A. et al., "High Quality 3D Laser Ranging Under General Vehicle Motion", 2008 IEEE International Conference on Robotics and Automation, May 19-23, 2008, pp. 7-12, XP031340123.
May, S. et al, "Robust 3D-Mapping with Time-of-Flight Cameras", Intelligent Robots and Systems, IROS 2009, IEEE/RSJ International Conference on Oct. 10, 2009, pp. 1673-1678, XP031581042.
Ohno, K. et al., "Real-Time Robot Trajectory Estimation and 3D Map Construction Using 3D Camera", Intelligent Robots and Systems, 2006 IEEE/RSJ International Conference on Oct. 1, 2006, pp. 5279-5285, XP031006974.
Surmann, H. et al., "An Autonomous Mobile Robot with a 3D Laser Range Finder for 3D Exploration and Digitalization of Indoor Environments", Robotics and Autonomous Systems, Elsevier Science Publishers, vol. 45, No. 3-4, Dec. 31, 2003, pp. 181-198.
Yan, R., et al, "3D Point Cloud Map Construction Based on Line Segments with Two Mutually Perpendicular Laser Sensors", 2013 13th International Conference on Control, Automation and Systems (ICCAS 2013), IEEE, Oct. 20, 2013, pp. 1114-1116.
Ye, C. et al., "Characterization of a 2-D Laser Scanner for Mobile Robot Obstacle Negotiation" Proceedings / 2002 IEEE International Conference on Robotics and Automation, May 11-15, 2002, Washington, D.C., May 1, 2002, pp. 2512-2518, XP009169742.
Chinese Office Action for Application No. 201280048465.3 dated Jul. 16, 2015; 10 pgs.
"Scanner Basis Configuration for Riegl VQ-250", Riegl Company Webpage, Feb. 16, 2011 [retrieved on Apr. 19, 2013]. Retrieved from the internet:, (see URL below).
14th International Forensic Science Symposium, Interpol—Lyon, France, Oct. 19-22, 2004, Review Papers, Edited by Dr. Niamh Nic Daeid, Forensic Science Unit, University of Strathclyde, Glasgow, UK.
ABB Flexible Automation AB: "Product Manual IRB 6400R M99, On-line Manual"; Sep. 13, 2006; XP00002657684; Retrieved from the Internet: URL: http://pergatory.mit.edu/kinematiccouplings/case_studies/ABB_Robotics/general/6400R%20Product%20Manual.pdf.
AKCA, Devrim, Full Automatic Registration of Laser Scanner Point Clouds, Optical 3D Measurement Techniques, vol. VI, 2003, XP002590305, ETH, Swiss Federal Institute of Technology, Zurich, Institute of Geodesy and Photogrammetry, DOI:10.3929/ethz-a-004656.
Anonymous : So wird's gemacht: Mit T-DSL und Windows XP Home Edition gemeinsam ins Internet (Teil 3) Internet Citation, Jul. 2003, XP002364586, Retrieved from Internet: URL:http://support.microsfot.com/kb/814538/DE/ [retrieved on Jan. 26, 2006]eh.
Bornaz, L., et al., "Multiple Scan Registration in Lidar Close-Range Applications," The International Archives of the Photogrammetry, Remote Sensing and Spatial Information Sciences, vol. XXXIV, Part 5/W12, Jul. 2003, pp. 72-77, XP002590306.
Bouvet, D., et al., "Precise 3-D Localization by Automatic Laser Theodolite and Odometer for Civil-Engineering Machines", Proceedings of the 2001 IEEE International Conference on Robotics and Automation. ICRA 2001. Seoul, Korea, May 21-26, 2001; IEEE, US.
Brenneke, C., et al., "Using 3D Laser Range Data for Slam in Outdoor Environments", Proceedings of the 2003 IEEE/RSJ International Conference on Intelligent Robots and Systems. (IROS 2003); Las Vegas, NV, Oct. 27-31, 2003; IEEE/RSJ International Confer.
Cho, et al., Implementation of a Precision Time Protocol over Low Rate Wireless Personal Area Networks, IEEE, 2008.
Cooklev, et al., An Implementation of IEEE 1588 Over IEEE 802.11b for Syncrhonization of Wireless Local Area Network Nodes, IEEE Transactions on Instrumentation and Measurement, vol. 56, No. 5, Oct. 2007.
Dylan, Craig R., High Precision Makes the Massive Bay Bridge Project Work. Suspended in MidAir—Cover Story—Point of Beginning, Jan. 1, 2010, [online] http://www.pobonline.com/Articles/Cover_Story/BNP_GUID_9-5-2006_A_10000000000 . . . [Retreived Jan. 25, 2002.
Electro-Optical Information Systems, "The Handy Handheld Digitizer" [online], [retrieved on Nov. 29, 2011], http://vidibotics.com/htm/handy.htm.
Elstrom, M.D., Stereo-Based Registration of LADAR and Color Imagery, Part of SPIE Conference on Intelligent Robots and Computer Vision XVII: Algorithms, Techniques, and Active Vision, Boston, MA, Nov. 1998, SPIE vol. 3522, 0277-786X/98; Retrieved on.
EO Edmund Optics "Silicon Detectors" (5 pages) 2013 Edmund Optics, Inc. http://www.edmundoptics.com/electro-optics/detector-components/silicon-detectors/1305[Oct. 15, 2013 10:14:53 AM].
FARO Laser Scanner LS, Recording Reality's Digital Fingerprint, the Measure of Success, Rev. Aug 22, 2005, 16 pages.
FARO Laserscanner LS, Presentation Forensic Package, Policeschool of Hessen, Wiesbaden, Germany, Dec. 14, 2005; FARO Technologies, Copyright 2008, 17 pages.

(56) References Cited

OTHER PUBLICATIONS

FARO Product Catalog; Faro Arm; 68 pages; Faro Technologies Inc. 2009; printed Aug. 3, 2009.
Franklin, Paul F., What IEEE 1588 Means for Your Next T&M System Design, Keithley Instruments, Inc., [on-line] Oct. 19, 2010, http://www.eetimes.com/General/DisplayPrintViewContent?contentItemId=4209746, [Retreived Oct. 21, 2010].
Gebre, et al. "Remotely Operated and Autonomous Mapping System (ROAMS)." Technologies for Practical Robot Applications, 2009. Tepra 2009. IEEE International Conference on IEEE, Piscataway, NJ, USA. Nov. 9, 2009, pp. 173-178.
GHOST 3D Systems, Authorized MicroScribe Solutions, FAQs—MicroScribe 3D Laser, MicroScan Tools, & related info, [online], [retrieved Nov. 29, 2011], http://microscribe.ghost3d.com/gt_microscan-3d_faqs.htm.
Godin, G., et al., A Method for the Registration of Attributed Range Images, Copyright 2001, [Retreived on Jan. 18, 2010 at 03:29 from IEEE Xplore].
GoMeasure3D—Your source for all things measurement, Baces 3D 100 Series Portable CMM from GoMeasure3D, [online], [retrieved Nov. 29, 2011], http://www.gomeasure3d.com/baces100.html.
Haag, et al., "Technical Overview and Application of 3D Laser Scanning for Shooting Reconstruction and Crime Scene Investigations", Presented at the American Academy of Forensic Sciences Scientific Meeting, Washington, D.C., Feb. 21, 2008.
Hart, A., "Kinematic Coupling Interchangeability", Precision Engineering, vol. 28, No. 1, Jan. 1, 2004, pp. 1-15, XP55005507, ISSN: 0141-6359, DOI: 10.1016/S0141-6359(03)00071-0.
Horn, B.K.P., Closed-Form Solution of Absolute Orientation Using Unit Quaternions, J. Opt. Soc. Am. A., vol. 4., No. 4, Apr. 1987, pp. 629-642, ISSN 0740-3232.
Howard, et al., "Virtual Environments for Scene of Crime Reconstruction and Analysis", Advanced Interfaces Group, Department of Computer Science, University of Manchester, Manchester, UK, Feb. 28, 2000.
Huebner, S.F., "Sniper Shooting Tecnhique", "Scharfschutzen Schiebtechnik", Copyright by C.A. Civil Arms Verlag GmbH, Lichtenwald 1989, Alle Rechte vorbehalten, pp. 11-17.
HYDROpro Navigation, Hydropgraphic Survey Software, Trimble, www.trimble.com, Copyright 1997-2003.
Information onElectro-Optical Information Systems; EOIS 3D Mini-Moire C.M.M. Sensor for Non-Contact Measuring & Surface Mapping; Direct Dimensions, Jun. 1995.
Ingensand, H., Dr., "Introduction to Geodetic Metrology", "Einfuhrung in die Geodatische Messtechnik", Federal Institute of Technology Zurich, 2004, with English translation.
iQsun Laserscanner Brochure, 2 Pages, Apr. 2005.
It is Alive in the Lab, Autodesk University, Fun with the Immersion MicroScribe Laser Scanner, [online], [retrieved Nov. 29, 2011], http://labs.blogs.com/its_alive_in_the_lab/2007/11/fun-with-the-im.html.
J.Geng "Structured-Light 3D Surface Imaging: A Tutorial," Advances in Optics and Photonics 3; Mar. 31, 2011, pp. 128-160; IEEE Intelligent Transportation System Society; 2011 Optical Society of America.
Jasiobedzki, Piotr, "Laser Eye—A New 3D Sensor for Active Vision", SPIE—Sensor Fusion VI, vol. 2059, Sep. 7, 1993, pp. 316-321, XP00262856, Boston, U.S.A., Retrieved from the Internet: URL:http://scitation.aip.org/getpdf/servlet/Ge.
Jasperneite, et al., Enhancements to the Time Synchronization Standard IEEE-1588 for a System of Cascaded Bridges, IEEE, 2004.
JGENG "DLP-Based Structured Light 3D Imaging Technologies and Applications" (15 pages) Emerging Digital Micromirror Device Based Systems and Application III; edited by Michael R. Douglass, Patrick I. Oden, Proc. of SPIE, vol. 7932, 79320B; (2011) SPIE.
Kreon Laser Scanners, Getting the Best in Cutting Edge 3D Digitizing Technology, B3-D MCAD Consulting/Sales [online], [retrieved Nov. 29, 2011], http://www.b3-d.com/Kreon.html.
Langford, et al., "Practical Skills in Forensic Science", Pearson Education Limited, Essex, England, First Published 2005, Forensic Chemistry.
Leica Geosystems TruStory Forensic Analysis by Albuquerque Police Department, 2006.
Leica Geosystems, FBI Crime Scene Case Study, Tony Grissim, Feb. 2006.
Leica Geosystems: "Leica Rugby 55 Designed for Interior Built for Construction", Jan. 1, 2009, XP002660558, Retrieved from the Internet: URL:http://www.leica-geosystems.com/downloads123/zz/lasers/Rugby%2055/brochures/Leica_Rugby_55_brochure_en.pdf [re.
Merriam-Webster (m-w.com), "Interface". 2012. http://www.merriam-webster.com/dictionary/interface.
Merriam-Webster (m-w.com), "Parts". 2012. http://www.merriam-webster.com/dictionary/parts.
Moog Components Group "Technical Brief; Fiber Optic Rotary Joints" Document No. 303 (6 pages) Mar. 2008; MOOG, Inc. 2008 Canada; FOCAL Technologies.
Patrick Willoughby; "Elastically Averaged Precision Alignment"; In: "Doctoral Thesis"; Jun. 1, 2005; Massachusetts Institute of Technology; XP55005620; Abstract 1.1 Motivation; Chapter 3, Chapter 6.
Romer Measuring Arms; Portable CMMs for the shop floor; 20 pages; Hexagon Metrology, Inc. (2009) http//us.ROMER.com.
Spada, et al., IEEE 1588 Lowers Integration Costs in Continuous Flow Automated Production Lines, XP-002498255, ARC Insights, Insight # 2003-33MD&H, Aug. 20, 2003.
Trimble—Trimble SPS630, SPS730 and SPS930 Universal Total Stations, [on-line] http://www.trimble.com/sps630_730_930.shtml (1 of 4), [Retreived Jan. 26, 2010 8:50:29AM].

\* cited by examiner

DEVICE FOR OPTICALLY SCANNING AND MEASURING AN ENVIRONMENT

CROSS REFERENCE TO RELATED APPLICATIONS

The present patent application is a National Stage Patent Application of, and which claims priority to, PCT Patent Application No. PCT/EP2012/075178, filed on Dec. 12, 2012, which claims the benefit of U.S. Provisional Patent Application No. 61/592,024, filed on Jan. 30, 2012, and of German Patent Application No. 10 2012 100 609.1, filed on Jan. 25, 2012, and all of which are hereby incorporated by reference herein.

BACKGROUND OF THE INVENTION

The invention relates to a device for optically scanning and measuring an environment.

By a laser scanner device, such as is known for example from German Patent Application No. DE 20 2006 005 643, the environment of the laser scanner can be optically scanned and measured.

SUMMARY OF THE INVENTION

Embodiments of the present invention are based on the object of improving a device of the type mentioned hereinabove.

Different operating modes can be provided for the laser scanner. In at least one operating mode (e.g., a helix mode), the laser scanner as a whole is moved by a cart on which the base of the laser scanner is mounted by a mounting device. The measuring head of the laser scanner rests relative to the base, while the mirror of the laser scanner rotates about its horizontal axis relative to the measuring head. The term "cart" may include any vehicle suitable for transporting the operating laser scanner.

According to embodiments of the present invention, in addition to a fixed connection between the base and the mounting device, the measuring head is locked together with the mounting device through use of corresponding first and second locking mechanisms. A pivot bearing between the measuring head and the base is thus bridged and relieved. In particular, static strains caused by a non-uniform clamping of the measuring head when the base is mounted on the mounting device and dynamic loads caused by moments of inertia of the measuring head are avoided.

A mechanical connection of the base with the mounting device and/or the locking of the measuring head with the mounting device may take place without backlash, for example by providing conical elements or elements which taper in a wedge-shaped manner. An electrical connection between the base and the mounting device may be optional and can be replaced, for example, by a direct connection (e.g., a cable) between the laser scanner, (for example, the base of the laser scanner) and the cart.

In another operating mode (e.g., a sphere mode) of the laser scanner, the base is stationary, and the mirror and the measuring head rotate about their axes.

A "horizontal" arrangement of the axis of rotation of the mirror and the "vertical" arrangement of the axis of rotation of the measuring head refer to an ideal alignment of the laser scanner. In case of an alignment of the laser scanner which is inclined with respect to the ideal alignment, the terms "horizontal" and "vertical" are interpreted in a relatively broader sense.

The components of the laser scanner may be arranged in two parts of the measuring head and in a traverse of the carrying structure which connects the two parts together. The carrying structure may form a part of the housing of the laser scanner, for example a bottom part and/or a central part between the two parts of the measuring head. To reduce the weight of the laser scanner, a shell may be provided as part of the housing, for example one shell each for each of the two parts of the measuring head, the shells comprising a relatively light material, for example plastic, and covering the corresponding components of the laser scanner for protection. To protect the shell, a yoke may be provided, for example one yoke for each shell, the yoke partially covering the outside of the shell and comprising a relatively light material as well, for example aluminum. The yokes can be omitted in alternative embodiments, for example if the shells are configured in a more stable manner and connected with the carrying structure.

The carrying structure which, for reasons of weight, may comprise aluminum as well, and may be provided with walls which fix the components with the optics and with the rotating mirror. The walls can also close the semi-open shells. The yoke may extend along the outer edges and/or obliquely over the outer surfaces of the shell and is fixed to the carrying structure, for example at the ends thereof, and if required also in the center thereof, at one of the two walls. In addition to the protective function, further functions can be integrated in the yokes.

The first locking mechanism, for example fixed notches, may be configured on the yokes. Also, a second locking mechanism may be provided, for example movable pawls, locks or similar, which are supported on the mounting device. The movable second locking mechanism then engages in the fixed first locking mechanism. The assignment of the fixed and of the movable locking mechanisms to the measuring head and to the mounting device, respectively, may also be reversed.

The mechanical connection of the base with the mounting device and the first locking mechanism between the measuring head and the mounting device may be arranged crosswise, to obtain a relatively stable support of the laser scanner on the mounting device. The terminal for the electrical connection with the cart may be located adjacent to the first locking mechanism and thus outside the space angle which can be reached by the emission light beam.

BRIEF DESCRIPTION OF THE DRAWINGS

The invention is explained in more detail below on the basis of an exemplary embodiment illustrated in the drawing, in which.

DETAILED DESCRIPTION OF THE INVENTION

Referring to FIGS. 1-4, a laser scanner 10 is provided as a device for optically scanning and measuring the environment of the laser scanner 10. The laser scanner 10 has a measuring head 12 and a base 14. The measuring head 12 is mounted on the base 14 as a unit that can be rotated about a vertical axis. The measuring head 12 has a rotary mirror 16, which can be rotated about a horizontal axis. The intersection point of the two axes of rotation is designated as the center $C_{10}$ of the laser scanner 10.

Figure 1:
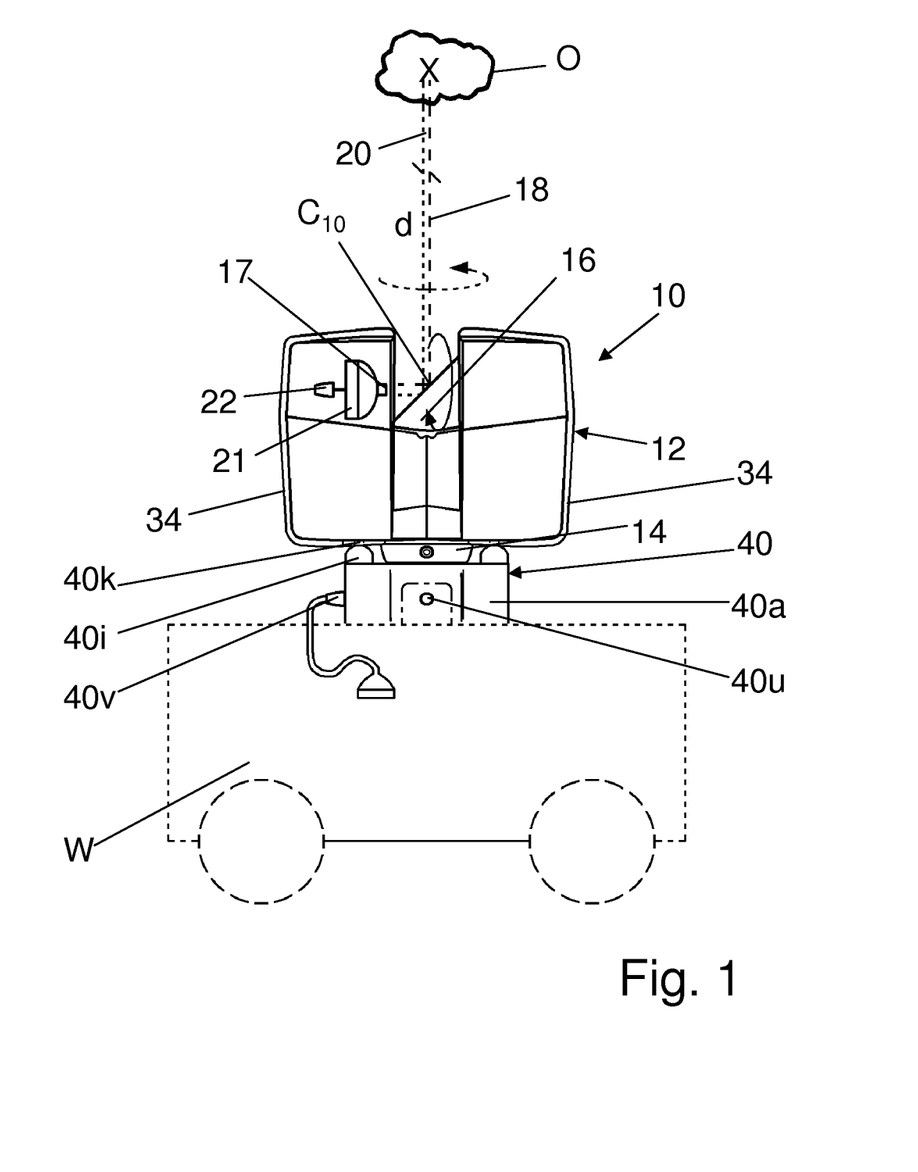
FIG. 1 is a schematic illustration of the laser scanner during operation, with a sketched cart.

The measuring head 12 is further provided with a light emitter 17 for emitting an emission light beam 18. The emission light beam 18 may be a laser beam in the range of approximately 300 to 1600 nm wave length, for example 790 nm, 905 nm or less than 400 nm; however, other electromagnetic waves having, for example, a greater wave length can be used. The emission light beam 18 is amplitude-modulated, for example with a sinusoidal or with a rectangular-waveform modulation signal. The emission light beam 18 is emitted by the light emitter 17 onto the rotary mirror 16, where it is deflected and emitted to the environment. A reception light beam 20 which is reflected in the environment by an object O or scattered otherwise, is captured again by the rotary mirror 16, deflected and directed onto a light receiver 21. The direction of the emission light beam 18 and of the reception light beam 20 results from the angular positions of the rotary mirror 16 and the measuring head 12, which depend on the positions of their corresponding rotary drives which, in turn, are registered by one encoder each.

A control and evaluation unit 22 has a data connection to the light emitter 17 and to the light receiver 21 in the measuring head 12, whereby parts of the unit 22 can be arranged also outside the measuring head 12, for example a computer connected to the base 14. The control and evaluation unit 22 determines, for a multitude of measuring points X, the distance d between the laser scanner 10 and the illuminated point at object O, from the propagation time of the emission light beam 18 and the reception light beam 20. For this purpose, the phase shift between the two light beams 18 and 20 can, for example, be determined and evaluated.

Scanning takes place along a circle by means of the relatively quick rotation of the rotary mirror 16. By virtue of the relatively slow rotation of the measuring head 12 relative to the base 14, the entire space is scanned step by step, by way of circles. The entity of measuring points X of such a measurement is designated as a scan. For such a scan, the center $C_{10}$ of the laser scanner 10 defines the origin of the local stationary reference system. The base 14 rests in this local stationary reference system.

In addition to the distance d to the center $C_{10}$ of the laser scanner 10, each measuring point X comprises a brightness information value which is determined by the control and evaluation unit 22 as well. The brightness value is a gray-tone value which is determined, for example, by integration of the bandpass-filtered and amplified signal of the light receiver 21 over a measuring period which is attributed to the measuring point X. A color camera can optionally generate pictures, by means of which colors (R, G, B) can be assigned to the measuring points as values.

A display device 24 is connected to the control and evaluation unit 22. The display device 24 is integrated into the laser scanner 10, in the present case into the measuring head 12. The display device 24 shows a preview of the scan.

Figure 2:
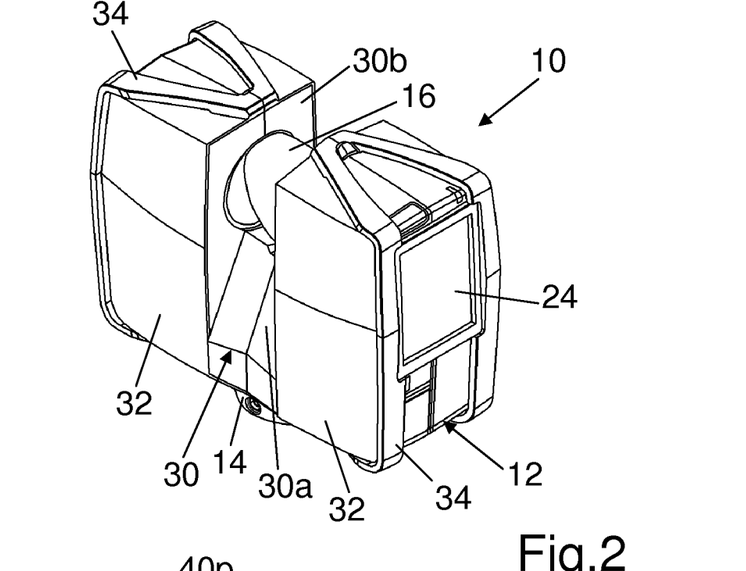
FIG. 2 is a perspective illustration of the laser scanner.

The laser scanner 10 has a carrying structure 30 which serves as a skeleton of the measuring head 12 and at which different components of the laser scanner 10 are fixed. In an exemplary embodiment, the metal carrying structure 30 is made of aluminum and in one piece. Above the base 14, the carrying structure 30 has a traverse 30a which is visible from the outside and which, at both ends, carries two walls 30b, which are parallel to one another and project upwards from the traverse 30a. Two shells 32 are configured as a housing which is open to one side. The shells 32 may comprise a plastic material. Each of the two shells 32 covers part of the components of the laser scanner 10 which are fixed to the carrying structure 30 and is assigned to one of the two walls 30b, to which it is fixed (e.g., sealed with a sealing material). The walls 30b and the shells 32 thus serve as a housing of the laser scanner 10.

On the outer side of each of the two shells 32 a yoke 34, which may comprise a metal material, is arranged, which partially covers and thus protects the corresponding shell 32. Each yoke 34 is fixed to the carrying structure 30, and more precisely on the bottom of the traverse 30a. In an exemplary embodiment, each yoke 34 is made of aluminum and is screwed to the traverse 30a at the side of the base 14. Each yoke 34 extends from its fixing point at the bottom of the traverse 30a obliquely to the next outer corner of the assigned shell 32, from where it extends along the outer edge of shell 32 to the outer corner of shell 32 which is above, on the upper side of shell 32 obliquely up to the wall 30b, a short distance along it, and then mirror-symmetrically to the described course on the upper side of shell 32, obliquely to the other outer corner, along the outer edge of shell 32 to the outer corner of shell 32 which is below and obliquely to the other fastening point at the bottom side of traverse 30a.

The two yokes 34 together circumscribe a convex space, within which the two shells 32 are completely arranged; i.e., the two yokes 34 together project over all outer edges and outer surfaces of the shells 32. On top and on the bottom the oblique sections of the yokes 34 project over the top and/or bottom of the shells 32, on the four other sides, two sections each extending along an outer edge of the shells 32. The shells 32 are thus protected extensively. Although each of the yokes 34 primarily has a protective function, particularly with respect to impacts which might damage the shells 32 and the components of the laser scanner 10 which are arranged below, further functions can be integrated in one or both of the yokes 34, for example a gripping possibility for carrying the laser scanner 10 and/or an illumination.

Further details of the design of the laser scanner 10 are described for example in German Patent Application No. DE 10 2009 055 988 B3, the relevant disclosure of which is expressly incorporated by reference herein.

In embodiments of the present invention, two different operating modes may be provided for the laser scanner 10.

In a sphere mode, the base 14 is arranged in the environment in a stationary manner, the mirror 16 rotates about its horizontal axis, and the measuring head 12 rotates about its vertical axis. The two rotations define a sphere, by which the laser scanner 10 scans its environment (e.g., completely).

In a helix mode, the base 14 moves relative to its environment along a line, the mirror 16 rotates about its horizontal axis, and the measuring head 12 rests relative to the base 14. The rotation and the movement along the line define a helix, by which the laser scanner 10 scans its environment (e.g., partially). On principle, the line can have any shape. However, the line may usually comprise straight and/or slightly curved sections.

For the helix mode, the laser scanner 10 is mounted on a cart W, for example on a motor vehicle. A mounting device 40 is provided for this purpose, which may be fixedly connected both mechanically and electrically with both the cart W and the laser scanner 10.

Figure 3:
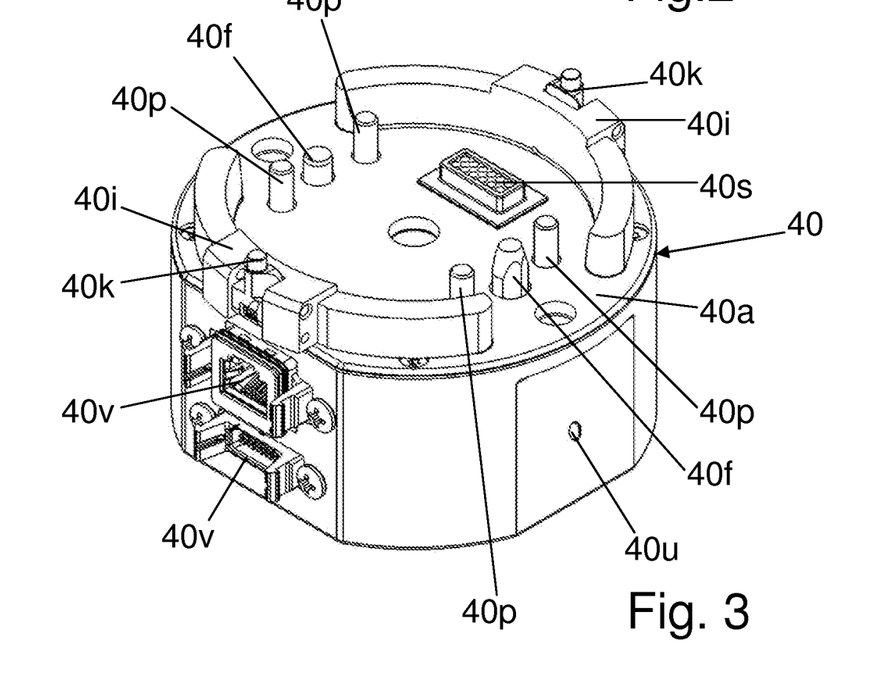
FIG. 3 is a perspective illustration of the mounting device.
Figure 4:
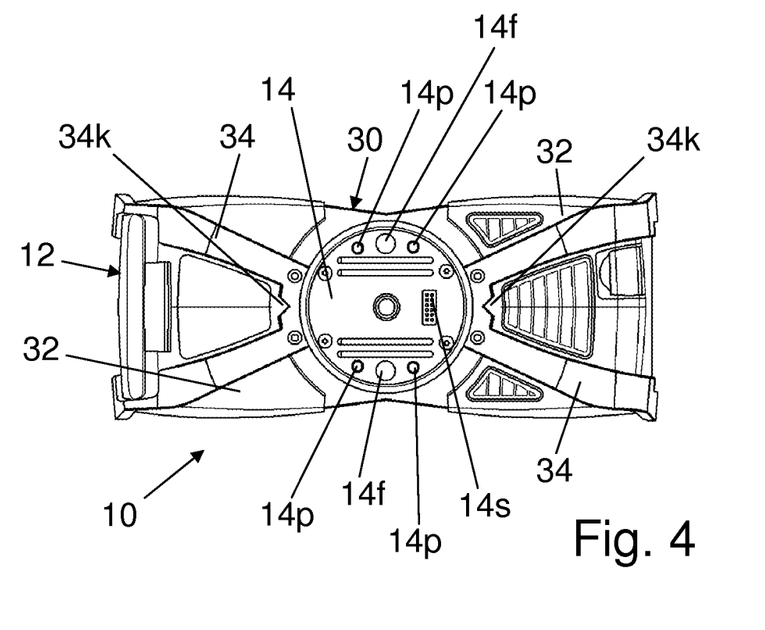
FIG. 4 is an underside view of the laser scanner.

In the exemplary embodiment, the mounting device 40 has an approximately cylindrical body 40a, the diameter of which is slightly bigger than that of the base 14. Two pairs of fixing pins 40p (e.g., rotatable screws) protrude from the upper face of the body 40a of the mounting device 40. The fixing pins 40p interact with suitable fixing holes 14p configured on the underside of the base 14. A pre-positioning by the fixing pins 40p may likely be subject to backlash. This is why, from the upper face of the mounting device 40, two additional positioning pins 40f protrude which interact with suitable positioning holes 14f on the underside of the base 14. Each of the positioning pins 40f is arranged between the two fixing pins 40p of a pair. When the fixing pins 40p enter the assigned fixing holes 14p (i.e., are screwed in), the positioning pins 40f enter the assigned positioning holes 14f. The positioning pins 40f are configured to be fixed relative to the basic body 40a. At least one of the two positioning pins 40f may have a conical end, which, when entering the assigned positioning hole 14f, provides for an absence of backlash and a force closure. In addition to the mechanical fixing elements, electrical connecting elements are provided, in an exemplary embodiment on the upper face of the body 40a, an integrated contact bushing 40s with flat contacts and on the underside of the base 14, an integrated mating contact plug 14s with spring pins.

On the circumferential surface of the body 40a, the mounting device 40 has at least two screw-in holes 40u (or alternatively other fixation means) for the mechanical connection with the cart W and at least one terminal for the electrical connection with the cart W. The electric connecting elements 14s, 40s and 40v allow for transmission of both data and energy. The assignments of male and female electric connecting elements to the base 14 and to the mounting device 40 can also be exchanged. The same applies to the mechanical connecting elements 14f, 14p and 40f, 40p.

The mounting device 40 is connected mechanically to the laser scanner 10 by the above-described mechanical connecting elements 14f, 14p, 40f and 40p (i.e., a mechanical connecting mechanism) at the base 14 of the laser scanner 10. The mounting device 40 is also connected electrically to the laser scanner 10 by the electric connecting elements 14s and 40s (i.e., an electrical connecting mechanism). In the event of an agitated movement of the cart W during the helix mode, the measuring head 12 with its inertia may stress with changing moments its pivot bearing in the base 14. According to embodiments of the present invention, the mounting device 40 therefore is not only fixedly connected with the base 14, but it is also locked with the measuring head 12. For this purpose, the mounting device 40 interacts with the yokes 34, and consequently with the carrying structure 30.

Each of the two yokes 34 has, in the immediate vicinity of the fixation of the yoke 34 to the carrying structure 30 (i.e., in an embodiment the screw points at the traverse 30a), a first locking mechanism 34k. The two first locking mechanisms 34k are thus fixed to the carrying structure 30. Each first locking mechanism 34k is configured, in an embodiment, as a notch in the yoke 34 with flanks which taper in a wedge-shaped manner, wherein the yoke 34 opens radially outward with respect to the axis of rotation of the measuring head 12. The two first locking mechanisms 34k thereby open in opposite directions. The two first locking mechanisms 34k can also be formed on the carrying structure 30 (i.e., configured in one piece with the structure 30) or may be separate components which are fixed to the yokes 34 or to other parts of the carrying structure 30.

The mounting device 40 has, on its body 40a and offset to each of the pairs of fixing pins 40p and positioning pins 40f, a pillow block 40i. The pillow blocks 40i are curved in an arc-shaped manner with an almost square cross section. The pillow blocks 40i, which may be configured in one piece, have in their center a central area, as well as wing areas on the sides thereof. The wing areas serve for fixing the corresponding pillow block 40i, relatively more precisely for receiving fixing screws. The wing areas may be omitted if the pillow block 40i is fixed in another manner. The central area is elevated with respect to the wing areas, so that the wing areas of the pillow blocks 40i are spaced from the yokes 34, if the base 14 bears on the upper face of the basic body 40a. For a pre-positioning, however, the central area of each pillow block 40i can be dimensioned in such a way that it engages between the assigned yokes 34.

Each pillow block 40i pivotably mounts a second locking mechanism 40k which, in an embodiment, may be configured as a pin-shaped lock with a support which bears it. The two second locking mechanisms 40k can pivot from a radial initial position with respect to the body 40a into an axial final position and back. A pre-bias of each of the two second locking mechanisms 40k is provided in the initial position and in the final position, for example by a spring which has a dead point between an initial position and a final position. In a modified embodiment, a pre-bias is provided only for the final position. The two second locking mechanisms 40k may be pivoted manually. Regarded from above, the positioning pins 40f and the second locking mechanisms 40k are arranged crosswise, i.e., the connection lines intersect, in an embodiment, at an angle of 90°. Alternative arrangements are possible, however. The at least one electrical connecting element 40v for the electrical connection with the cart W may be located adjacent to the second locking mechanisms 40k, in an embodiment below the central area of one of the pillow blocks 40i and consequently outside the space angle which is reached by the emission light beam 18.

To connect the mounting device 40 with the laser scanner 10, the scanner 10 is placed with its base 14 on the body 40a and is positioned by the positioning pins 40f and the positioning holes 14f, without backlash in the final position. At the same time, the contact plug 14s is plugged into the contact bushing 40s. The fixing pins 40p then are moved, i.e., screwed into the fixing holes 14p, the base 14 thus being connected without backlash with the mounting device 40. Finally the two second locking mechanisms 40k are pivoted into their final position. Shortly before reaching the final position, they approach from the radial direction the corresponding one of the two first locking mechanisms 34k which are configured as notches and finally engage therein, if necessary by sliding along the flanks of the notches (e.g., the flanks being tapered in a wedge-shaped manner), until the measuring head 12 is locked without backlash with the mounting device 40.

A completely strain-free locking may be achieved by the measuring head 12 being aligned as precisely as possible with respect to its angle position relative to the base 14 at the latest before the two second locking mechanisms 40k are pivoted into their final position, so that, by both the two first locking mechanisms 34k and the two second locking mechanisms 40k, only the backlash of the rotary drive of the measuring head 12 needs to be eliminated or reduced. Since the angle position of the measuring head 12 is registered by an encoder, a calibration of the encoder may be advantageous. Alternatively, a smoothly running idle movement of the rotary drive or a relatively large backlash of the same can be provided, so that the two first and second locking mechanisms 34k and 40k themselves carry out the relatively precise alignment of the measuring head 12.

What is claimed is:

1. A laser scanner device for optically scanning and measuring an environment, the laser scanner comprising a base, a measuring head which is rotatable relative to the base, and a mirror which is rotatable relative to the measuring head, wherein the measuring head includes a carrying structure configured as a frame of the measuring head, wherein the laser scanner is mounted on a cart by a mounting device, the cart moves the base which is fixedly connected with the mounting device via a first mechanical connecting mechanism and a first electrical connecting mechanism provided on a bottom side of the base and via a second mechanical connecting mechanism and a second electrical connecting mechanism provided on an upper face of the mounting device, the measuring head rests relative to the base, and the mirror rotates, wherein the measuring head includes at least a first locking mechanism that is fixed to the carrying structure, wherein the mounting device supports at least a second locking mechanism, wherein the measuring head is locked with the mounting device by engagement of the first locking mechanism and the second locking mechanism.

2. The device of claim 1, wherein as part of a housing of the laser scanner, at least one shell is provided on the measuring head, the outside of the shell being partly covered by at least one yoke configured to protect and being fixed to the carrying structure.

3. The device of claim 2, wherein the at least one first locking mechanism is configured on the yoke in the form of a notch which, with respect to an axis of rotation of the measuring head, points radially outwards.

4. The device of claim 1, wherein the mounting device has at least one pillow block, which pivotably supports the second locking mechanism.

5. The device of claim 1, wherein the mounting device has a body on the face of which the base bears with its bottom side and on which the second mechanical and electrical connecting mechanisms are arranged.

6. The device of claim 4, wherein the pillow block is arranged on an upper face of the body.

7. The device of claim 1, wherein the measuring head includes a light emitter that emits an emission light beam which is deflected into the environment by the mirror, and a light receiver that receives a reception light beam which is reflected by an object in the environment or scattered otherwise, the device further comprising a control and evaluation unit that determines, for a multitude of measuring points each, at least the distance to the object.

* * * * *